US008518664B2

(12) United States Patent
Roscoe et al.

(10) Patent No.: US 8,518,664 B2
(45) Date of Patent: Aug. 27, 2013

(54) METHODS OF DETERMINING THE AMOUNT OF MICROORGANISMS PRESENT IN A TEST SAMPLE

(75) Inventors: Stephen B. Roscoe, Woodbury, MN (US); Phillip A. Bolea, Grant, MN (US); Stephanie J. Moeller, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/513,794

(22) PCT Filed: Dec. 17, 2010

(86) PCT No.: PCT/US2010/060936
§ 371 (c)(1),
(2), (4) Date: Jun. 4, 2012

(87) PCT Pub. No.: WO2011/087711
PCT Pub. Date: Jul. 21, 2011

(65) Prior Publication Data
US 2012/0252049 A1    Oct. 4, 2012

Related U.S. Application Data

(60) Provisional application No. 61/288,883, filed on Dec. 22, 2009.

(51) Int. Cl.
*C12Q 1/04* (2006.01)
(52) U.S. Cl.
USPC .................................................. 435/34
(58) Field of Classification Search
USPC .................................................. 435/34
See application file for complete search history.

(56) References Cited

U.S. PATENT DOCUMENTS

| | | | |
|---|---|---|---|
| 4,591,554 A | | 5/1986 | Koumura |
| 5,079,144 A | * | 1/1992 | Carr et al. ................. 435/32 |
| 5,354,655 A | * | 10/1994 | Ward et al. ................ 435/6.11 |
| 6,372,895 B1 | | 4/2002 | Bentsen |
| 6,387,650 B1 | | 5/2002 | Townsend |
| 6,472,167 B1 | | 10/2002 | Townsend |
| 6,566,508 B2 | | 5/2003 | Bentsen |
| 2002/0147317 A1 | * | 10/2002 | Bentsen et al. ................. 536/8 |
| 2007/0190593 A1 | * | 8/2007 | Abbaszadegan et al. ....... 435/34 |

FOREIGN PATENT DOCUMENTS

WO    WO 2004/027084    4/2004

OTHER PUBLICATIONS

Chilvers, "Synthesis and Evaluation of Novel Fluorogenic Substrates for the Detection of Bacterial β-galactosidase", Journal of Applied Microbiology, Dec. 2001, vol. 91, No. 6, pp. 1118-1130.
Gee, "Fluorogenic Substrates Based on Fluorinated Umbelliferones for Continuous Assays of Phosphatases and β-Galactosidases", Analytical Biochemistry, Aug. 1999, vol. 273, No. 1, pp. 41-48.
Koller, "Photometric and Fluorometric Continuous Kinetic Assay of Acid Phosphatases with New Substrates Possessing Longwave Absorption and Emission Maxima", Analytical Biochemistry, Nov. 1984, vol. 143, No. 1, pp. 146-151.
Manafi, "Fluorogenic and Chromogenic Substrates Used in Bacterial Diagnostics", Microbiological Reviews, Sep. 1991, vol. 55, No. 3, pp. 335-348.
Orenga, "Enzymatic Substrates in Microbiology", Journal of Microbiological Methods, Nov. 2009, vol. 79, No. 2, pp. 139-155.
Perry, "Evaluation of Novel Fluorogenic Substrates for the Detection of Glycosidases in *Escherichia coli* and enterococci", Journal of Applied Microbiology, Jul. 2006, vol. 101, No. 5, pp. 977-985.
Sicart, "Fluorogenic substrates for lipases, esterases, and acylases using a TIM-mechanism for signal release", Biotechnology Journal, Jan. 2007, vol. 2, No. 2, pp. 221-231.
Sun, "Synthesis of Novel Fluorinated Coumarins: Excellent UV-Light Excitable Fluorescent Dyes", Bioorganic & Medicinal Chemistry Letters, Nov. 1998, vol. 8, No. 22, pp. 3107-3110.
Sungur, "Immobilisation of β-Galactosidase onto Gelatin by Glutaraldehyde and Chromium(III) Acetate", Journal of Chemical Technology and Biotechnology, Feb. 1994, vol. 59, No. 3, pp. 303-306.
Wolfbeis, "PH-Dependent Fluorescence Spectra of 3-Substituted Umbelliferones", Naturforsch, 1977, vol. 32a, pp. 1065-1067.
Yang, "A Novel Fluorogenic Coumarin Substrate for Monitoring Acid Phosphatase Activity at Low pH Environment", Current Chemical Genomics, 2008, vol. 2, pp. 48-50.
International Search Report for PCT/US2010/060936, 4 pages.

* cited by examiner

*Primary Examiner* — Ralph Gitomer
(74) *Attorney, Agent, or Firm* — Stephen L. Crooks

(57) ABSTRACT

Methods of determining the amount of microorganisms present in a test sample. The methods include a) incubating the test sample with a growth media to form an incubated sample, wherein the growth media includes an enzyme substrate and the enzyme substrate includes an enzymatically hydrolyzable group and a fluorescent group, wherein microorganisms present in the test sample include an enzyme that hydrolyzes the hydrolyzable group from the fluorescent group to form a fluorescently detectable product, wherein the fluorescently detectable product has both an acidic and basic species; b) exciting the fluorescently detectable product with light having a wavelength of Ex$\lambda$iso for a time sufficient for the fluorescently detectable product to emit light, wherein Ex$\lambda$iso is the absorbance isosbestic point of the fluorescently detectable product; c) detecting light emitted at a wavelength of Em$\lambda$1; and d) quantifying the light emitted at the wavelength of Em$\lambda$1, wherein the quantity of the light emitted at the wavelength Em$\lambda$1 is indicative of the amount of microorganisms present in the test sample.

18 Claims, 17 Drawing Sheets

METHODS OF DETERMINING THE AMOUNT OF MICROORGANISMS PRESENT IN A TEST SAMPLE

CROSS REFERENCE TO RELATED APPLICATIONS

This application is a national stage filing under 35 U.S.C. 371 of PCT/US2010/060936, filed Dec. 17, 2010, which claims priority to U.S. Provisional Application No. 61/288,883, filed Dec. 22, 2009, the disclosure of which is incorporated by reference in its/their entirety herein.

TECHNICAL FIELD

The present disclosure relates to methods of detecting microorganisms utilizing fluorogenic compounds.

BACKGROUND 7-hydroxycoumarin-based dyes (also called umbelliferones) and their derivatives are widely used as indicators for enzyme activity. One example of an umbelliferone is 4-methylumbelliferone (referred to as 4-MU), which is used for the detection of coliforms, amongst other things. The highest fluorescence of 4-MU (and other umbelliferones) is observed from the basic form, therefore such detection has to be undertaken at a pH of 8 to 10.

SUMMARY

There are numerous situations in which a detection response is desired at lower pH values. For example, kinetic studies of acid phosphatases require real-time detection of enzyme activity in acidic media. The ability to observe fluorescence at acidic pHs would also eliminate necessary steps in protocols, thereby making analyses quicker and easier. Because of the desire to carry out low pH fluorescence analysis, there remains a need for analysis methods that can be carried out irrespective of pH.

Disclosed herein is a method of detecting microorganisms in a test sample, the method including the steps of: a) incubating the test sample with an enzyme substrate to form an incubated sample, wherein the enzyme substrate includes an enzymatically hydrolysable group and a fluorescent group, wherein microorganisms present in the test sample include an enzyme that hydrolyzes the hydrolysable group from the fluorescent group to form a fluorescently detectable product, wherein the fluorescently detectable product has both an acidic and basic species; b) exciting the fluorescently detectable product with light having a wavelength of $Ex\lambda iso$ for a time sufficient for the fluorescently detectable product to emit light, wherein $Ex\lambda iso$ is the absorbance isosbestic point of the fluorescently detectable product; and c) detecting light emitted at a wavelength of $Em\lambda 1$.

Also disclosed is a method of detecting microorganisms in a test sample, the method including the steps of: a) incubating the test sample with an enzyme substrate, wherein the enzyme substrate includes an enzymatically hydrolysable group and a fluorescent group, wherein microorganisms present in the test sample include an enzyme that hydrolyzes the hydrolysable group from the fluorescent group to form a fluorescently detectable product, wherein the fluorescently detectable product has both an acidic and basic species; b) exciting the fluorescently detectable product with light having a wavelength of $Ex\lambda iso$ for a time sufficient for the fluorescently detectable product to emit light, wherein $Ex\lambda iso$ is the isosbestic point of the fluorescently detectable product; c) detecting light emitted at a wavelength of $Em\lambda 1$ as a result of the excitation with light having a wavelength of $Ex\lambda iso$; d) exciting the fluorescently detectable product with light having a wavelength of $Ex\lambda 2$ for a time sufficient for the fluorescently detectable product to emit light, wherein $Ex\lambda 2$ is the absorption maximum of the basic species of the fluorescently detectable product or the absorption maximum of the acidic species of the fluorescently detectable product; e) detecting light emitted at a wavelength of $Em\lambda 1$ as a result of the excitation with light having a wavelength of $Ex\lambda 2$; and f) calculating a ratio based on the light emitted as a result of the $Ex\lambda iso$ excitation light and the light emitted as a result of the $Ex\lambda 2$ excitation light, wherein the ratio is indicative of the amount of microorganisms present in the test sample.

Also disclosed is a kit for testing for the presence of microorganisms in a test sample, the kit including: enzyme substrate that includes an enzymatically hydrolysable group and a fluorescent group, wherein microorganisms present in the test sample include an enzyme that hydrolyzes the hydrolysable group from the fluorescent group to form a fluorescently detectable product wherein the fluorescently detectable product has both an acidic and basic species; and a light source capable of providing light having a wavelength of $Ex\lambda iso$, wherein $Ex\lambda iso$ is the isosbestic point of the fluorescently detectable product, and wherein excitation of the fluorescently detectable product with light having a wavelength of $Ex\lambda iso$ causes the fluorescently detectable product to emit light.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
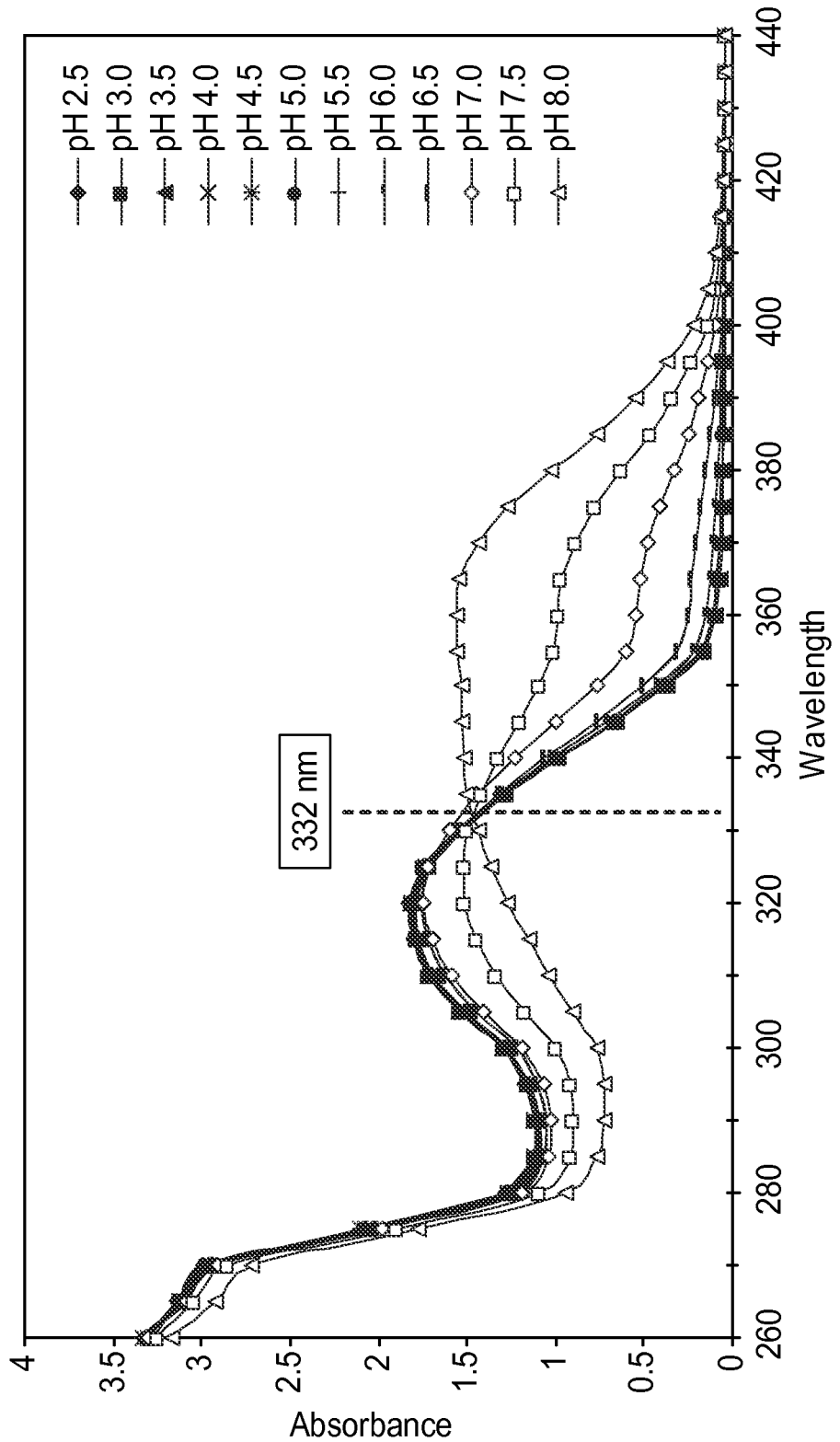
FIGS. 1A, 1B, and 1C are the absorption spectra of 4-methylumbelliferone (4-MU) for different pH values (FIG. 1A), the emission (excitation 455 nm) as a function of pH for two different excitation wavelengths (FIG. 1B), and emission spectra from 400 nm to 500 for different pH values (FIG. 1C)

In the following description, reference is made to the accompanying drawing that forms a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Disclosed herein are methods and kits for detecting microorganisms in samples. In embodiments, a method may generally include the steps of incubating the test sample with the enzyme substrate, irradiating the incubated sample with a first wavelength, and detecting light emitted from the sample. An enzyme substrate is a compound that can be cleaved by an enzyme of a microorganism, forming a fluorescently detectable product. The fluorescently detectable product is then irradiated at a wavelength of the isosbestic point of the fluorescently detectable product. Upon excitation of the fluorescently detectable product, the fluorescently detectable product will emit light, which can then be detected to confirm the presence of the microorganism in the test sample.

In embodiments, microorganisms that can be detected using methods and kits as disclosed herein can include bacteria, and fungi for example. Exemplary fungi include both yeasts (including for example, *Saccharomyces cerevisiae*, *Cryptococcus neoformans*, *Candida albicans*, *Candida tropicalis*, *Candida stellatoidea*, *Candida glabrata*, *Candida krusei*, *Candida parapsilosis*, *Candida guilliermondii*, *Candida viswanathii*, *Candida lusitaniae*, and *Rhodotorula mucilaginosa*) and molds (including for example, *Acremonium*, *Aspergillus*, *Cladosporium*, *Fusarium*, *Mucor*, *Penicillium*, *Rhizopus*, *Stachybotrys*, and *Trichoderma*) for example. Exemplary bacteria include the following microorganisms: *Aeromonas hydrophilia*, *Aeromonas caviae*, *Aeromonas sobria*, *Bacillus cereus*, *Bacillus stearothermophilus*, *Bacillus subtilis*, *Bacillus sphaericus*, *Bacteroides fragilis*, *Bacteroides intermedium*, *Citrobacter freundii*, *Clostridium perfringens*, *Enterobacter aerogenes*, *Enterobacter cloacae*, *Enterococcus faecium*, *Enterococcus faecalis*, *Escherichia coli*, *Haemophilus influenzae*, *Haemophilus parainfluenzae*, *Klebsiella pneumoniae*, *Lactococcus lactis*, *Listeria monocytogenes*, *Listeria innocua*, *Mycobacterium fortuitum*, *Neisseria gonorrhoeae*, *Organella morganii*, *Peptostreptococcus anaerobius*, *Peptococcus magnus*, *Proteus mirabilis*, *Pseudomonas aeruginosa*, *Pseudomonas fluorescens*, *Pseudomonas pudita*, *Salmonella typhimurium*, *Serratia liquefaciens*, *Serratia marcescens*, *Staphylococcus aureus*, *Staphylococcus epidermidis*, *Staphylococcus hominis*, *Staphylococcus simulans*, *Streptococcus agalactiae* B, *Streptococcus anginosus*, *Streptococcus constellatus*, *Streptococcus faecalis* D, *Streptococcus mutans*, *Streptococcus pyogenes*, *Streptococcus uberis*, and *Xanthomonas maltophilia*.

Types of samples that can be tested using methods and kits as disclosed herein (which can be referred to as "test samples") are generally not limited. Exemplary types of samples include clinical samples, environmental samples, food samples, cosmetics, beverage samples, water samples and soil samples. Alternatively, samples can be prepared from articles by rinsing the article to form a water sample to be tested, for example. Samples such as food samples and soil samples can be digested or subjected to other processing before disclosed methods and kits are utilized to detect microorganisms. Filtering treatments, extraction treatments and the like can also be carried out. In embodiments where a test sample is incubated with enzyme substrate, but not growth media, pre-processing of a sample could include incubating the sample with growth media and then adding the resultant solution (as the test sample) to the enzyme substrate.

The test sample can be incubated with an enzyme substrate. The enzyme substrate can be provided in or with growth media for example. Growth media generally are liquids or gels that are designed to support the growth of microorganisms. Exemplary growth media include nutrient broths, and agar plates. The growth media can be supplied as a liquid, a condensed or dehydrated liquid, or a gel for example. An example of a product that supplies growth media for use via hydration is 3M™ Petrifilm™ plates (3M Co., St. Paul, Minn.).

Incubating the test sample with the enzyme substrate (or enzyme substrate and growth media) can be accomplished simply by mixing the two; by mixing the two and allowing the mixture to sit; by mixing the two and agitating the mixture; by mixing the two and heating the mixture; or by mixing the two, agitating the mixture and heating the mixture. The step of incubating can be undertaken for any amount of time. In embodiments, the test sample and enzyme substrate are allowed to incubate at elevated temperatures until at least one cell division process has taken place.

In embodiments, the test sample and enzyme substrate (or enzyme substrate and growth media) can be mixed and then agitated using any commonly utilized mechanical agitation methods. The test sample and enzyme substrate can be mixed and then heated using any commonly utilized heating methods. In embodiments, the test sample and growth media can be mixed and agitated using commonly utilized methods. For example, microorganisms may be detected using 3M™ Petrifilm™ plates. The Petrifilm™ plate, which contains dehydrated growth media and enzyme substrate, is rehydrated with the test sample, which contains the microorganisms of interest. After addition of the test sample, the rehydrated Petrifilm™ plate can be incubated at suitable conditions to enable detection of microorganisms (for example, for an aerobic count, the 3M™ Petrifilm™ plates can be placed in an incubator at 37° C. for 24-48 hours; or for yeast/mold, the 3M™ Petrifilm™ plates can be placed in an incubator at 25 to 28° C. for 3 to 5 days).

An enzyme substrate as used herein is a material that is selectively hydrolysable by an enzyme to generate a fluorescently detectable product when cleaved. An enzyme substrate generally includes two portions, an enzymatically hydrolysable group (which can, but need not be a biological molecule) and a fluorescent group. An enzyme substrate can be pictorially represented by formula I below:

Hydrolysable Group ------------- Fluorescent Group      (Formula I)

In formula I, the moiety represented by "-------------" can be referred to as an enzymatically hydrolysable linkage. An enzymatically hydrolysable linkage refers to a linkage or bond that can easily be cleaved by an enzyme; particularly an enzyme produced by a microorganism of interest.

The fluorescent group can be fluorescently detectable once it is cleaved from the enzyme substrate. It should also be noted that the enzyme substrate can be fluorescently detectable before the fluorescent group is cleaved from it (or stated another way, the fluorescent group can be fluorescently detectable either within the enzyme substrate or cleaved from the enzyme substrate). In embodiments, the enzyme substrate can include a fluorescent dye joined to a moiety, which is cleavable by an enzyme produced by the microorganism of interest.

The hydrolysable group included in an enzyme substrate can include a glycone, a glycosyl phosphate, an ester, an amino acid or peptide, a phosphate, or a sulfate for example.

Exemplary glycone or glycosyl phosphates include α- and β-D-galactopyranosyl, α- and β-D-glucopyranosyl, N-acetyl-α- and β-D-galactosaminyl; N-acetyl-α- and β-glucosaminyl; β-D-glucuronyl, α-L-arabinopyranosyl, α-L-arabinofuranosyl, β-D-fucopyranosyl, α- and β-L-fucopyranosyl, α-D-mannopyranosyl, β-D-xylopyranosyl, α-D-maltosyl, β-D-lactopyranosyl, β-D-cellobiosyl, α-D-N-acetylneuraminyl, and myoinositol-1-yl phosphate. In embodiments, the hydrolysable group can include α- and β-D-galactopyranosyl, α- and β-D-glucopyranosyl, or β-D-glucuronyl. In embodiments, the hydrolysable group includes β-D-galactosyl or β-D-glycosyl.

Exemplary esters include butyrate, valerate, hexanoate, caprylate, octanoate, nonanoate, and palmitate. An exemplary ester can include a long chain ester of umbelliferone, such as 4-methylumbelliferylpalmitate, 4-methylumbelliferyllaurate, 4-methylumbelliferylcaprylate, which are commercially available (such hydrolysable groups can be used to detect esterase or palmitase). Furthermore, enzyme substrates that are hydrolysable by lipase, esterase, acylase and epoxide hydrolase can also be utilized, including those referred to in Sicart et al., Biotechnology Journal, 2007 2(2), 221-231.

Exemplary amino acids can include carboxy terminal-linked amino acids or an acid addition salt thereof. Such amino acids can include N-acetyl-L-lysine, L-alanine, L-arginine, L-aspartic acid, N-alpha-benzyloxycarbonyl-L-arginine, L-citrulline, gamma-L-glutamic acid, L-glycine, L-histidine, L-hydroxyproline, L-isoleucine, L-leucine, L-lysine, L-methionine, L-ornithine, L-phenylalanine, L-proline, L-pyroglutamic acid, L-serine, L-tryptophan, L-tyrosine, and L-valine. Exemplary peptides can include carboxy terminal-linked peptides having 1 to 4 amino acids or an addition salt thereof. Such peptides can include L-arginyl-L-arginine, N-benzyloxycarbonyl-glycyl-L-proline, L-glutaryl-glycyl-arginine, glycyl-glycine, glycyl-L-phenylalanine, glycyl-L-proline, and L-seryl-L-tyrosine. In embodiments, the hydrolysable group is a terminal-linked peptide having 1 to 4 amino acids, wherein free amino groups optionally have a protective group, or an acid addition salt thereof.

Any fluorescent dye possessing a pH-dependent absorption and an isosbestic point (or fluorogenic portion thereof) can be utilized in enzyme substrates utilized herein. Exemplary fluorescent dyes include xanthene derivatives (such as fluorescein, rhodamine and derivatives thereof), cyanine derivatives (such as cyanine, indocarbocyanine, oxacarbocyanine, thiacarbocyanine and merocyanine and derivatives thereof), naphtalene derivatives, coumarin derivatives, oxadiazole derivatives, pyrene derivatives, oxazine derivatives, acridine derivatives, arylmethine derivatives, and tetrapyroole derivatives.

In embodiments, coumarin derivatives can be utilized in enzyme substrates. Exemplary coumarin derivatives include 7-hydroxycoumarin (umbelliferone) derivatives. Specific 7-hydroxycoumarin derivatives include 4-methyl-7-hydroxycoumarin (4-methylumbelliferone or 4-MU), 3-cyano-7-hydroxycoumarin (3-cyanoumbelliferone or CyU), and 7-hydroxycoumarin-3-carboxylic acid esters such as ethyl-7-hydroxycoumarin-3-carboxylate (EHC), methyl-7-hydroxycoumarin-3-carboxylate (MHC), 3-cyano-4-methylumbelliferone, 3-(4-imidazolyl)umbelliferone, and 6,8-difluoro-4-methylumbelliferone. 7-hydroxycoumarin derivatives such as those containing a 5-membered heterocyclic ring at the 3-position can also be utilized in fluorogenic compounds herein. Such 7-hydroxycoumarin derivatives are exemplified in U.S. Pat. No. 6,566,508 (Bentsen et al.), the disclosure of which is incorporated herein by reference thereto. A specific example of such a derivative is 3-(2-thienyl)umbelliferone (TU).

Exemplary enzyme substrates include, but are not limited to 4-methylumbelliferone-β-D-galactopyranoside (MUG), 3-cyanoumbelliferone-β-D-galactopyranoside, 7-hydroxycoumarin-3-carboxylic acid ethyl ester-β-D-galactopyranoside, 7-hydroxycoumarin-3-carboxylic acid methyl ester-β-D-galactopyranoside, 3-(2-thienyl)umbelliferone-β-D-galactopyranoside, 4-methylumbelliferyl phosphate, 3-cyanoumbelliferyl phosphate, ethyl umbelliferone-3-carboxyl phosphate, methyl umbelliferone-3-carboxyl phosphate, 3-(2-thienyl)umbelliferyl phosphate, 5-bromo-4-chloro-3-indolyl-beta-D-galactopyranoside (X-gal), 5-Bromo-4-chloro-3-indolyl phosphate (BCIP), ELF 97 Acetate (Invitrogen, Carlsbad, Calif.), ELF 97 Beta D Glucuronide (Invitrogen, Carlsbad, Calif.), and ELF 97 Beta D Galactopyranoside (Invitrogen, Carlsbad, Calif.).

The fluorescently detectable product has both an acidic and a basic species. Generally, the acidic species of a fluorescently detectable product is a compound that can donate a hydrogen ion ($H^+$) to another component in solution; and a basic species of a fluorescently detectable product is a compound that can accept a hydrogen ion ($H^+$) from another component in solution. In embodiments, a fluorescently detectable product has an acidic species that is neutral and a basic species that is anionic. In embodiments, a fluorescently detectable product has an acidic species that is cationic and a basic species that is neutral.

The acidic and basic species of a fluorescently detectable product can absorb light differently (either in the amount of energy absorbed, the wavelength, or both), can emit light differently (either in intensity, the wavelength of emission, or both) or can both absorb and emit light differently. FIG. 1A shows the absorbance spectra of solutions of 4-methylumbelliferone (4-MU) at pHs from 2.5 to 8.0. As seen there, the absorbance varies greatly across the monitored wavelength range (260 nanometers to 440 nanometers). At a wavelength of about 332 nanometers (nm), the absorbance does not significantly vary across the entire pH range. This wavelength, 332 nm for 4-MU, is referred to herein as the excitation isosbestic point. The excitation isosbestic point is the wavelength at which the absorbance of the acidic and basic species of the fluorescently detectable product is substantially the same. The excitation isosbestic point of a fluorescently detectable product is also referred to herein as Ex$\lambda$iso.

Excitation of a solution containing a fluorescently detectable product at the excitation isosbestic point (Ex$\lambda$iso) can provide a pH independent fluorescent response. In embodiments, an incubated sample can be irradiated with light having a wavelength of Ex$\lambda$iso. In embodiments, light having a wavelength of Ex$\lambda$iso can refer to light that has a peak wavelength of ±10 nm of Ex$\lambda$iso. In embodiments, light having a wavelength of Ex$\lambda$iso can refer to light that has a peak wavelength of ±5 nm of Ex$\lambda$iso. In embodiments, light having a wavelength of Ex$\lambda$iso can refer to light that has a peak wavelength of ±2 nm of Ex$\lambda$iso.

The incubated sample can be irradiated with light having a wavelength of Ex$\lambda$iso for an amount of time that is sufficient for the fluorescently detectable product to emit light. In embodiments, the incubated sample can be irradiated with light having a wavelength of Ex$\lambda$iso for fractions of a second to tens of seconds. In embodiments, the incubated sample can be irradiated with light having a wavelength of Ex$\lambda$iso for about a second to tens of seconds. In embodiments that can be utilized with the 3M™ Attest™ Biological Monitoring System (3M Co., St. Paul, Minn.), a sample can be irradiated for about a second, which can be sufficient time to obtain a stably excited sample and integrate the intensity of emissions. In embodiments that can be utilized with the 3M™ Petrifilm™ plate system (3M Co., St. Paul, Minn.), a sample can be irradiated for tens of seconds, which can be sufficient time to integrate the emission intensity to obtain a detectable signal above background noise.

After the incubated sample is irradiated with light having a wavelength of Ex$\lambda$iso for a sufficient time, the fluorescently detectable product will emit light. Irradiation of a fluorescently detectable product with a wavelength of light that it absorbs can be referred to as excitation. Excitation at a wavelength other than Ex$\lambda$iso causes the acidic and basic species to absorb differently, and therefore the light emitted will also be different. This behavior yields a pH sensitive fluorescent response from most fluorescently detectable products. An example of this phenomenon can be seen in FIG. 1B. The line designated 140 shows the fluorescence (at 455 nm) of 4-methylumbelliferone (4-MU) with excitation at 360 nm at various pHs from 2.5 to 8.0. As seen there, the fluorescence changes dramatically across this pH range. Beginning at a pH of 6, the fluorescence begins to increase substantially. For this reason, it is generally accepted that fluorescence measurements of 4-MU should be done at a basic pH (usually from a pH of 8 to 10) with an excitation wavelength of about 360 nm so that a maximum fluorescence signal is obtained.

Figure 1B:
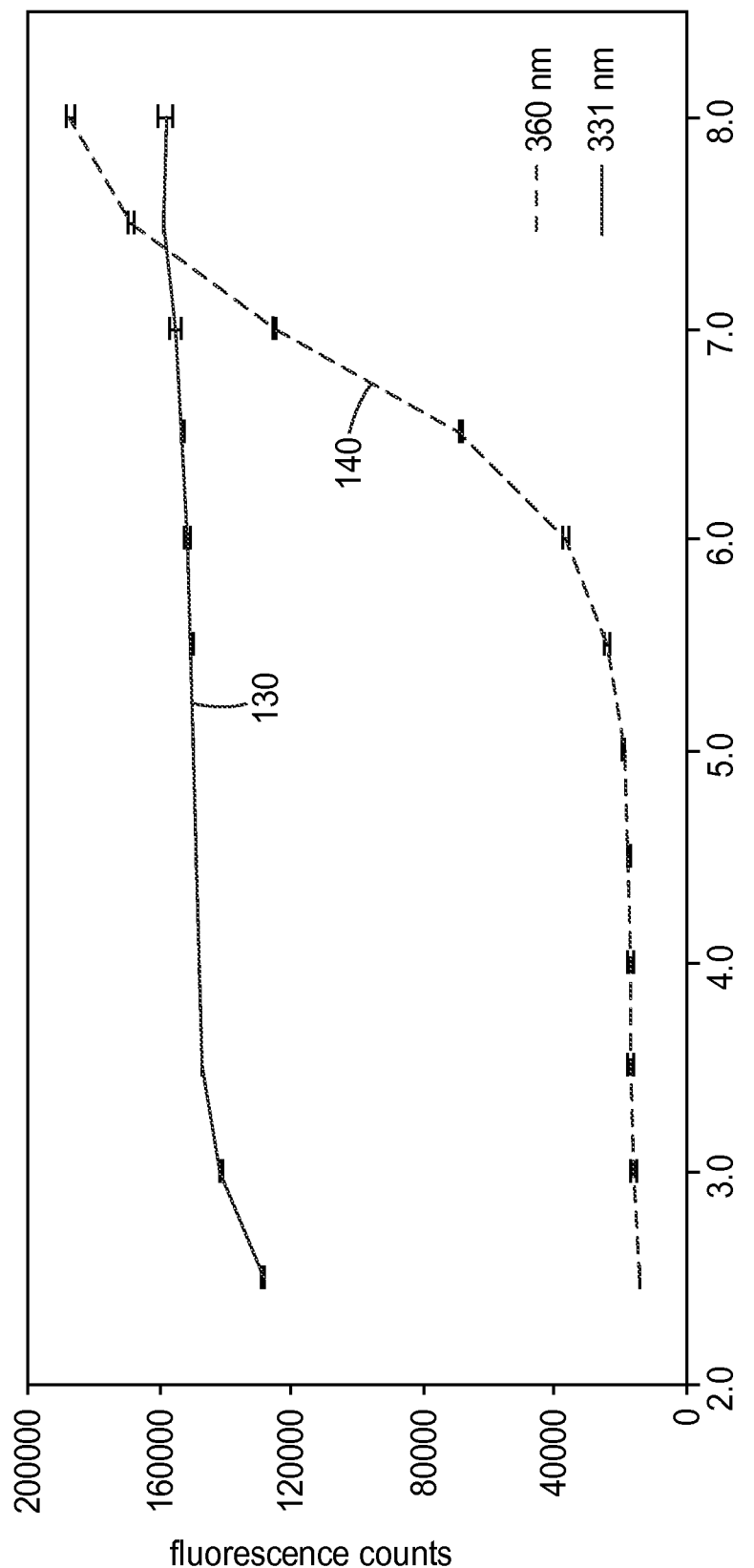

The line designated 130 in FIG. 1B shows the fluorescence (at 455 nm) of 4-MU with excitation at 330 nm at various pHs from 2.5 to 8.0. As seen there, the fluorescence is almost constant across this pH range. The combination of the results of FIG. 1A, showing that the excitation isosbestic point (Ex$\lambda$iso) of 4-MU is about 332 nm; and the results of FIG. 1B, showing that the fluorescence (at 455 nm) is substantially constant across the pH range of 2.5 to 8.0 shows that excitation of a sample at the excitation isosbestic point (Ex$\lambda$iso) can provide a pH independent fluorescence response.

Figure 1C:
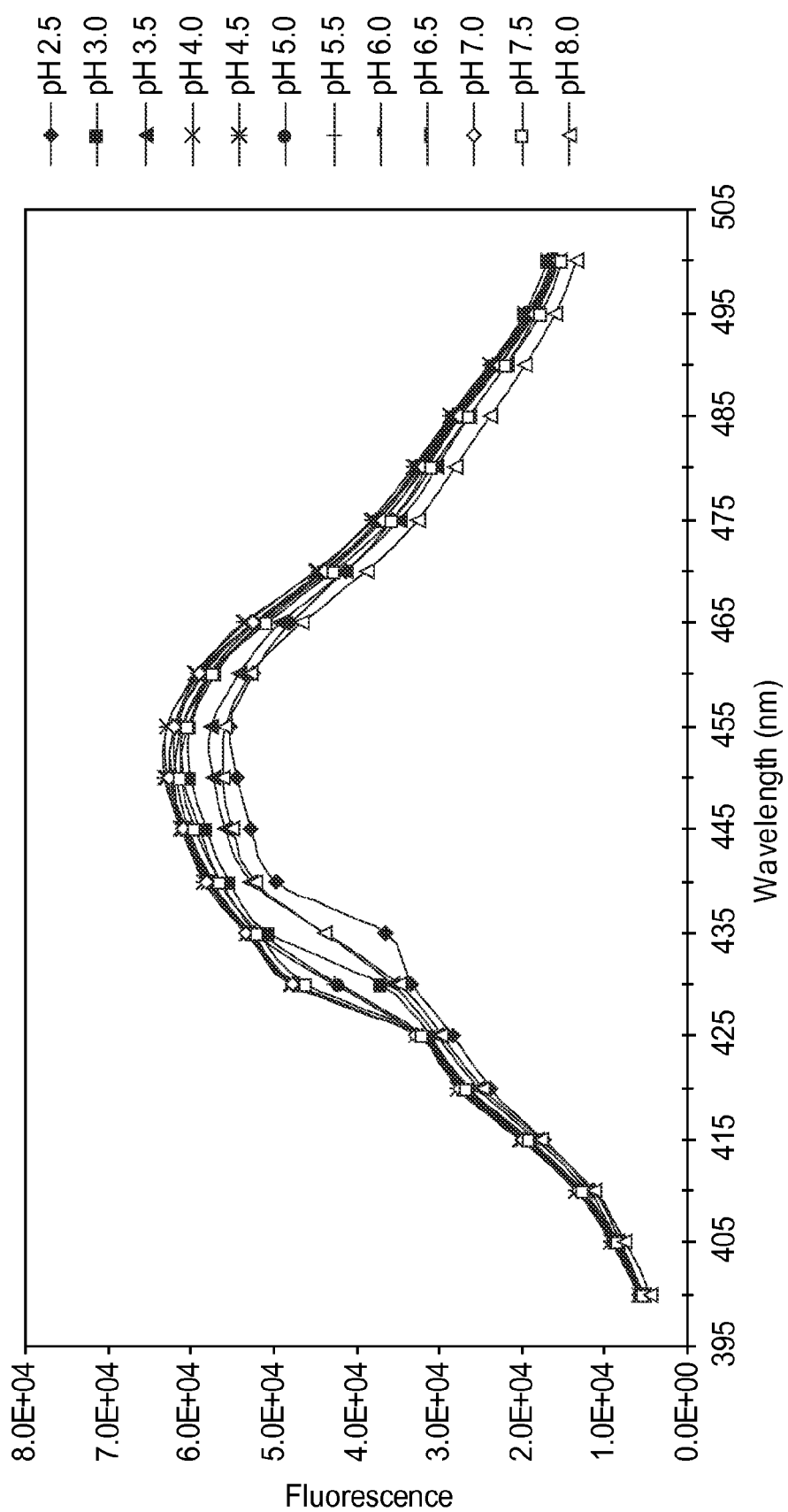

FIG. 1C shows an emission sweep (from 400 nm to 500 nm) of solutions of 4-MU at pHs from 2.5 to 8.0 after excitation at 330 nm. As shown in FIG. 1C, the fluorescent response is also independent of pH in that the wavelength of emission also does not vary with pH. This phenomenon can be due to photodissociation of the neutral species (in the case of 4-MU, the acidic species) followed by proton transfer to the solvent resulting in a photogenerated anion (in the case of 4-MU, the basic species) which then emits at its characteristic wavelength.

Some exemplary fluorescently detectable products and their excitation isosbestic points are as follows: 4-methylumbelliferone (4-MU) has an excitation isosbestic point (Ex$\lambda$iso) of about 330 nm; 3-cyano-7-hydroxycoumarin (CyU) has an excitation isosbestic point (Ex$\lambda$iso) of about 375 nm; 7-hydroxycoumarin-3-carboxylic acid ethyl ester (EHC) has an excitation isosbestic point (Ex$\lambda$iso) of about 370 nm; 7-hydroxycoumarin-3-carboxylic acid methyl ester (MHC) has an excitation isosbestic point (Ex$\lambda$iso) of about 370 nm; and 3-(2-thienyl)umbelliferone (TU) has an excitation isosbestic point (Ex$\lambda$iso) of about 380 nm.

Using 4-MU as an example, shifting the excitation frequency from the commonly utilized 360 nm to about 330 nm (Ex$\lambda$iso) can eliminate the 20 to 30 fold decrease in fluorescence intensity when going from pH 8 to pH 5. This intensity decrease can be eliminated in disclosed methods without requiring further steps (e.g. pH adjustment).

A pH independent fluorescence response can provide advantages in various analysis methods. For example, the step of adjusting the pH of the test sample to be analyzed (which step is necessary in numerous previously utilized methods) to a pH of 8 to 10 can be eliminated. This can render the analysis easier, more efficient, and more cost effective. For example, various types of bacteria, including for example *E. Coli, Lactobacillus*, and *acetobacter*, generate acids as they grow, a pH independent response will ensure that results are not influenced by such acids. For example, samples having varying acidity levels can be tested without the need to "neutralize" them prior to testing. For example, a relatively large difference between the excitation and emission wavelengths can allow the use of inexpensive optical filters (for example absorption filters as opposed to more expensive narrow band interference filters). For example, higher signal to noise ratios can be provided because of greater Stokes shifts and associated tails crossing.

Excitation of the incubated sample can be accomplished using any light source capable of providing light having the appropriate wavelength (e.g. Ex$\lambda$iso). Exemplary light sources can include a visible laser diode, a visible light emitting diode (LED), an incandescent filament, or any other suitable light source. The light source can also be combined with various filters and other optics as are commonly utilized.

In embodiments, a light source can be chosen so that a relatively insubstantial amount of light is present at the emission detection wavelength. This can be advantageous because it can minimize the amount of detected light that is due to the excitation source. Alternatively, optics can be used to filter out a portion of the light from the excitation light source. In embodiments, an excitation light source, optics, the wavelength of detection, a detector, or some combination thereof are chosen so that substantially no light from the excitation light source is detected and/or attributed to being an emission from a fluorescently detectable product.

Once the fluorescently detectable product has been excited with light having a wavelength of Ex$\lambda$iso for a time sufficient for the fluorescently detectable product to emit light, the emitted light is then detected. In embodiments, the emitted light can be detected within at least about a couple of minutes of exciting the fluorescently detectable product. In embodiments, the emitted light can be detected within at least about a minute of exciting the fluorescently detectable product. In embodiments that utilize silicon based sensors (a common choice for NIR ranges up to 1000 nm), integration times can be about a minute if a single stage thermal electric cooling (TEC) is used to cool the sensor to about 30° below ambient temperatures.

Detection of the light emitted by the excited fluorescently detectable product can be accomplished as is generally known. Detectors, such as photomultiplier tubes, avalanche photodiodes, charge coupled devices (CCDs), photodiodes, or other active devices for example, may be utilized. The detector can also be combined with various filters and other optics as are commonly utilized.

The wavelength of emitted light to be detected can depend at least in part on the particular fluorescently detectable product. As seen in FIG. 1C, a fluorescently detectable product (such as 4-MU for example) emits light, in various quantities, over a wide range of wavelengths. In embodiments, the emission can be detected at a wavelength that is close to the maximum emission. Alternatively, other wavelengths (in addition to or in place of the wavelength of maximum emission) can be monitored in order to detect the emitted light. Em$\lambda$1 can be any desired wavelength, and can be chosen based in part on the intensity of the emissions at various wavelengths, the particular detector (cost, etc.) that can be utilized, interference from other components in the sample (for example the enzyme substrate), or a combination thereof. In embodiments, Em$\lambda$1 can be the wavelength at which the fluorescently detectable product has its maximum intensity emissions. Such an Em$\lambda$1 can be useful to minimize possible interference from background signals, decrease detection limits, or a combination thereof. Whatever wavelength is chosen to monitor emission, it can be referred to herein as the emission wavelength, or Em$\lambda$1.

In embodiments, an enzyme substrate can be chosen that has a Ex$\lambda$iso and a maximum emission (which can be utilized as Em$\lambda$1) that are substantially far apart in terms of wavelength (nanometers). In embodiments, an enzyme substrate can be chosen that has a Ex$\lambda$iso and a maximum emission (as Em$\lambda$1) that are at least about 20 nm apart. In embodiments, an enzyme substrate can be chosen that has a Ex$\lambda$iso and a maximum emission (as Em$\lambda$1) that are at least about 30 nm apart. In embodiments, an enzyme substrate can be chosen that has a Ex$\lambda$iso and a maximum emission (as Em$\lambda$1) that are at least about 40 nm apart.

The particular wavelength at which emission is monitored (Em$\lambda$1) can also be chosen based in part on emission of the enzyme substrate. For example, in embodiments where the enzyme substrate absorbs at the isosbestic point but has an emission spectra that is different from the fluorescently detectable product, excitation at Ex$\lambda$iso along with detection at Em$\lambda$1, where Em$\lambda$1 is chosen so that the enzyme substrate does not emit (or does not substantially emit), can be advantageous. Such a scenario allows for pH independent detection of the fluorescently detectable product but not the enzyme substrate. Different fluorescently detectable products (and/or different enzyme substrates) can render different wavelengths more advantageous for use as Em$\lambda$1. In embodiments, 4-methylumbelliferone $\beta$-D-galactopyranoside (4-MUG), 7-hydroxycoumarin-3-carboxylic acid methyl ester-$\beta$-D-galactopyranoside (MHCgal), or 7-hydroxycoumarin-3-carboxylic acid ethyl ester-$\beta$-D-galactopyranoside (EHCgal) can be excited at Ex$\lambda$iso and the fluorescently detectable product can be detected (Em$\lambda$1) at a commonly utilized wavelength, 455 nm without substantial detection of the enzyme substrate.

Once the emitted light has been detected (at Em$\lambda$1), various additional steps can optionally be carried out. One optional step is that the emitted light can be quantified in order to estimate the amount of microorganisms in the test sample. This can be accomplished by comparing the integrated intensity of emitted light from the test sample with the integrated intensity of emitted light (under the same conditions) from one or more than one standard samples having known quantities of microorganisms. A relative comparison can also be carried out by, for example, comparing the fluorescent intensity at two different times (for example before and after a sterilization procedure).

Another additional step that can optionally be carried out is to form an image of the detected light. In an embodiment, a CCD (or other detector) that has a number of individually addressable photosensitive detector elements can enable the collection of fluorescent data from the sensor or sensor array on a pixel by pixel basis. This array can be used in combination with an illumination source and proper collection optics to obtain an image of, for example sites of growing microbial colonies on an inoculated two dimensional surface (for example a 3M™ Petrifilm™ plate) that includes enzyme substrates as disclosed herein. The resulting electronic image can be transmitted to the processor assembly, where image analysis software can be used to enhance the contrast of the image and to count the number of fluorescent spots automatically (or a user can count the number of spots manually).

Figure 2:
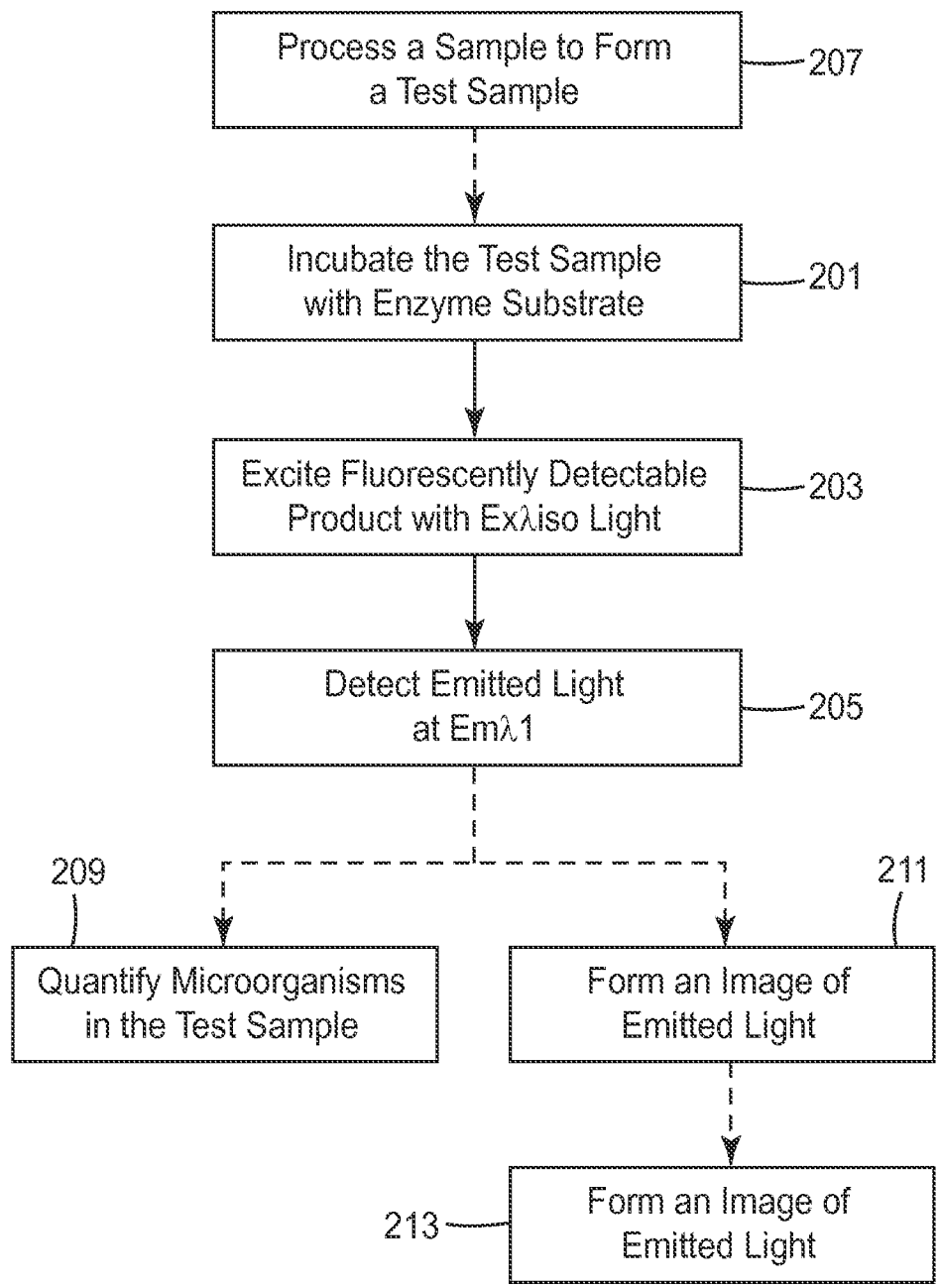
FIG. 2 is a flowchart depicting exemplary methods disclosed herein.

FIG. 2 depicts exemplary embodiments of methods disclosed herein. Embodiments of disclosed methods can include step 201, incubating a test sample with enzyme substrate, step 203, exciting a fluorescently detectable product within the incubated test sample with light having a wavelength of Ex$\lambda$iso, and step 205, detecting the emitted light at Em$\lambda$1.

An optional step, step 207, may be added to such a method before step 201. Step 207 includes processing a sample to form a test sample; as discussed above, such processing can include filtering, digesting, extracting, and the like.

Another optional step, step 209, may be added to such a method after step 205. Step 209 includes quantifying the microorganisms in the test sample; as discussed above, such quantification can include use of samples of known concentrations of microorganisms for example, or can be a relative comparison (i.e., obtaining a more or less than result).

Another optional step, step 211, may be added to such a method after step 205. Step 211 includes forming an image of the emitted light; as discussed above, formation of an image can include use of addressable detectors and collection optics. In embodiments where step 211 is carried out, the method can further include step 213, which can be carried out after step 211. Step 213 includes counting microorganism colonies from the image; as discussed above, such colony counting can be done automatically by a processor in communication with the image forming electronics or can be done manually by a user.

It should also be noted that any combination of the above discussed steps can be carried out in methods disclosed herein. Furthermore, any combination of discussed steps can be repeated using different test samples (or the same test sample).

Methods disclosed herein can also include steps of irradiating the incubated samples at wavelengths in addition to Exλiso. One such example includes irradiating the incubated sample at a wavelength of Exλ2 for a time sufficient for the fluorescently detectable product to emit light. The wavelength referred to herein as Exλ2 can be the absorption maximum of the basic species of the fluorescently detectable product, the absorption maximum of the acidic species of the fluorescently detectable product, or some other wavelength. For example, the fluorescently detectable product 4-MU, has an absorption maximum of the basic species at about 360 nm, and an absorption maximum of the acidic species at about 320 nm; the fluorescently detectable product CyU has an absorption maximum of the basic species of about 405 nm, and an absorption maximum of the acidic species at about 355 nm.

Excitation at Exλiso and Exλ2 for times sufficient to cause the fluorescently labeled product to emit light can cause emissions of the same wavelength (it should also be noted that emissions at different wavelengths may also occur). In embodiments, excitation at Exλiso and Exλ2 are not done at the same time, but are separated in time. Detection of the independent emitted light (caused by excitation at Exλiso and Exλ2) can also occur separated in time. Once the separate emissions (caused by excitation at Exλiso and Exλ2) are detected they can be utilized in various different ways. In embodiments, the two emissions can be utilized in the same fashion, as a way of double checking the results.

In embodiments, the two emissions can be utilized to determine a dimensionless number that can be utilized to provide a response that does not depend on measuring absolute fluorescent intensity. This can be accomplished by determining a ratio that is the ratio of the emission caused by Exλiso and the emission caused by Exλ2. The numerator and denominator choice is irrelevant; however if the choice remains constant, the ratio can be used to compare results from sample to sample.

In embodiments, another relative method can be utilized whereby variation in the excitation intensity (Exλiso) can be compensated for by monitoring the excitation intensity while integrating the emission signal (Emλ1). Such an embodiment can be utilized along with the 3M™ Attest™ Biological Monitoring System. In embodiments of such a method utilized along with the 3M™ Attest™ Biological Monitoring System, the two groups of data can be mathematically processed in a microprocessor in the 3M™ Rapid Attest™ Autoreader™ (3M Co., St. Paul, Minn.).

In embodiments, exciting the incubated sample at two different excitation wavelengths (Exλiso and Exλ2) can be utilized to not only determine the amount of microorganism in the test sample but also to monitor the pH of the incubated sample over time. Such is the case because Exλ2 in essence monitors the amount of the acidic or basic species (assuming that a wavelength where at least one or the species absorbs is utilized as Exλ2) as a function of time. Monitoring the pH can be another method of monitoring microorganism growth, metabolic activity, or a combination thereof.

Figure 3:
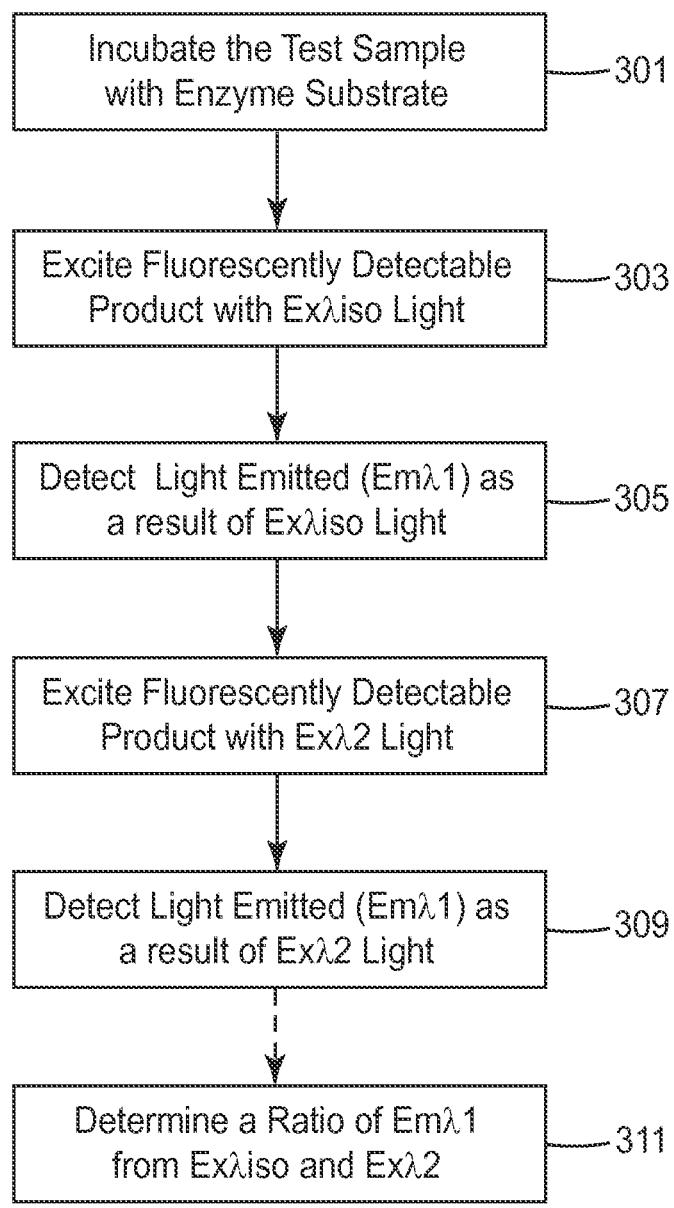
FIG. 3 is a flowchart depicting exemplary methods disclosed herein.

FIG. 3 depicts exemplary embodiments of methods disclosed herein. Embodiments of disclosed methods can include step 301, incubating a test sample with enzyme substrate, step 303, exciting a fluorescently detectable product within the incubated test sample with light having a wavelength of Exλiso, step 305, detecting the light emitted (Emλ1) as a result of Exλiso, step 307, exciting a fluorescently detectable product within the incubated test sample with light having a wavelength of Exλ2, and step 309, detecting the light emitted (Emλ1) as a result of Exλ2. In embodiments, step 307 and step 309 can be performed prior to steps 303 and 305.

An optional step, step 311, may be added to such a method after step 309. Step 311 includes determining a ratio of the emission caused by Exλiso and the emission caused by Exλ2. Such a ratio can serve the purpose of providing a dimensionless number that is not based on fluorescent intensity. Optional steps such as those discussed above with respect to FIG. 2 may also be included in methods such as those exemplified in FIG. 3. It should also be noted that any combination of the above discussed steps can be carried out in methods disclosed herein. Furthermore, any combination of discussed steps can be repeated using different test samples (or the same test sample).

In embodiments, the ratio of the emission at Exλiso and Exλ2 can indicate things other than the amount of organisms in the sample. In embodiments where the enzyme substrate emits strongly when excited at Exλiso (for example, TUgal), the ratio of the emission at Exλiso and Exλ2 can indicate the amount of organisms present because the ratio will be largely invariant with enzymatic activity (unlike excitation near the anion max). In embodiments where there is minimal interference from the enzyme substrate at either excitation frequency (Exλiso and Exλ2) then the ratio of emission from Exλiso and Exλ2 can indicate a pH level. For some organisms that generate acid, a change in pH is indicative of their presence.

Methods disclosed herein can also include optional steps of detecting different wavelengths of emission. As discussed above, once the sample is irradiated with light having a wavelength of Exλiso, the fluorescently detectable product will emit light. As seen in FIG. 1C, for example, the fluorescently detectable product can emit light across a wide range of wavelengths. Methods disclosed herein include a step of detecting emitted light of a wavelength of Emλ1, such methods can optionally include a further step of detecting emitted light at a second, different wavelength. The additional wavelength of emitted light that can be detected is referred to herein as Emλ2.

Emλ2 can be any desired wavelength, and can be chosen based in part on the intensity of the emissions at various wavelengths, the particular detector (cost, etc.) that can be utilized, interference from other components in the sample (for example the enzyme substrate), the wavelength of Emλ1 or a combination thereof. In embodiments, Emλ2 can be the wavelength at which the fluorescently detectable product has its maximum intensity emissions (if such a wavelength were not utilized as Emλ1). Such an Emλ2 can be useful to minimize possible interference from background signals, decrease detection limits, or a combination thereof. In embodiments, Emλ2 can be the wavelength at which the emission of the fluorescently detectable product is independent of pH, or stated another way the isosbestic emission point (Emλiso). Such an Emλ2 can be useful to compensate for a weak photoacid that has significant emission from the acidic and basic species, which would otherwise give a pH dependent response.

In embodiments, Emλ2 is chosen so that the amount of light emitted by the fluorescently detectable product is at least greater than the amount of light emitted by the enzyme substrate. In embodiments, Emλ2 is chosen so that the amount of light emitted by the fluorescently detectable product is substantially greater than the amount of light emitted by the enzyme substrate. Such an Emλ2 can be useful to minimize the background interference from the enzyme substrate that has not been cleaved by enzymes within microorganisms.

In embodiments, detection at $Em\lambda 1$ and $Em\lambda 2$ are not done at the same time, but are separated in time. Excitation of the fluorescently detectable product (by $Ex\lambda$iso for example) can also occur separated in time. The emissions at $Em\lambda 1$ and $Em\lambda 2$ can be utilized in various different ways. In embodiments, the two emissions can be utilized in the same fashion, as a way of double checking the results.

In embodiments, the two emissions can be utilized to determine a dimensionless number that can be utilized to provide a response that does not depend on measuring absolute fluorescent intensity. This can be accomplished by determining a ratio that is the ratio of the emission at $Em\lambda 1$ and the emission at $Em\lambda 2$. The numerator and denominator choice is irrelevant; however if the choice remains constant, the ratio can be used to compare results from sample to sample.

Figure 4:
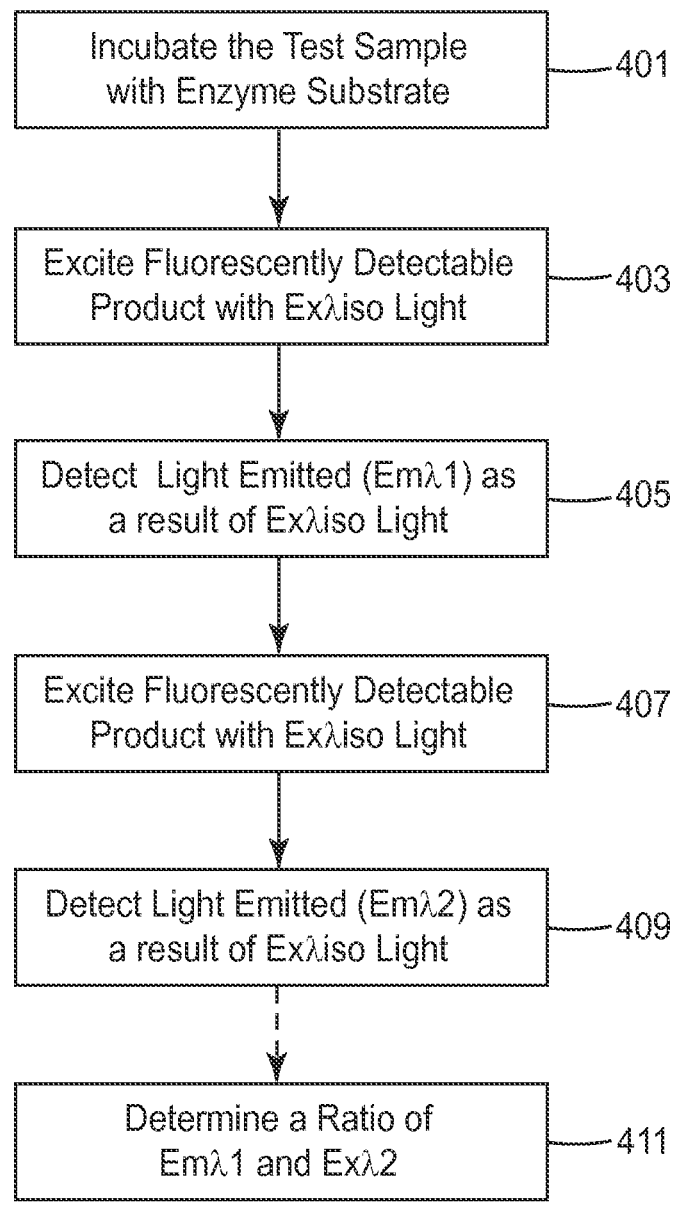
FIG. 4 is a flowchart depicting exemplary methods disclosed herein.

FIG. 4 depicts exemplary embodiments of methods disclosed herein. Embodiments of disclosed methods can include step 401, incubating a test sample with enzyme substrate, step 403, exciting a fluorescently detectable product within the incubated test sample with light having a wavelength of $Ex\lambda$iso, step 405, detecting the light emitted at $Em\lambda 1$ as a result of $Ex\lambda$iso, step 407, exciting a fluorescently detectable product within the incubated test sample with light having a wavelength of $Ex\lambda$iso, and step 409, detecting the light emitted at $Em\lambda 2$ as a result of $Ex\lambda$iso.

An optional step, step 411, may be added to such a method after step 409. Step 411 includes determining a ratio of $Em\lambda 1$ and $Em\lambda 2$. Optional steps such as those discussed above with respect to FIG. 2 may also be included in methods such as those exemplified by FIG. 4. It should also be noted that any combination of the above discussed steps can be carried out in methods disclosed herein. Furthermore, any combination of discussed steps can be repeated using different test samples (or the same test sample).

Kits are also disclosed herein. Kits as disclosed herein can include enzyme substrate, and a light source. The enzyme substrate as discussed above can be included in disclosed kits. Generally, the enzyme substrate includes an enzymatically hydrolysable group and a fluorescent group, wherein microorganisms present in the test sample include an enzyme that hydrolyzes the hydrolysable group from the fluorescent group to form a fluorescently detectable product wherein the fluorescently detectable product has both an acidic and basic species. In embodiments, the enzyme substrate can be more specifically defined as above. In embodiments, the enzyme substrate can be included as a component of growth media which can also be included in a disclosed kit.

Kits as disclosed herein also include a light source. The light source is at least capable of providing light having a wavelength of $Ex\lambda$iso. Exemplary light sources can include a visible laser diode, a visible light emitting diode (LED), an incandescent filament, an organic light emitting diode (OLED), or any other suitable light source. In embodiments, inexpensive LEDs can be utilized as a light source within disclosed kits. The light source can also be combined with or used in combination with various filters and optics as are commonly utilized.

The light source included in the kit can also be capable of providing light having a wavelength of $Ex\lambda 2$, where $Ex\lambda 2$ can be the absorption maximum of the basic species of the fluorescently detectable product, the absorption maximum of the acidic species of the fluorescently detectable product, or some other wavelength. Alternatively a second light source capable of providing light having a wavelength of $Ex\lambda 2$ can be included in disclosed kits. In the latter embodiments, the kit can include at least two light sources, one capable of providing light having a wavelength of $Ex\lambda$iso; and a second capable of providing light having a wavelength of $Ex\lambda 2$, where $Ex\lambda 2$ can be the absorption maximum of the basic species of the fluorescently detectable product, the absorption maximum of the acidic species of the fluorescently detectable product, or some other wavelength.

Kits as disclosed herein can also include containers configured to mix at least the enzyme substrate and the sample to be tested. In embodiments, the optional container can come preloaded with the enzyme substrate; or in embodiments, the optional container can come preloaded with a growth media containing the enzyme substrate. An example of a container that can be preloaded with a growth media containing the enzyme substrate is 3M™ Petrifilm™ plates (3M Co., St. Paul, Minn.). Another example of a container that can be preloaded with a growth media containing enzyme substrate is 3M™ Attest™ Biological Monitoring System (3M Co., St. Paul, Minn.). Alternatively, a container can optionally be provided along with separately packaged enzyme substrate, whether mixed with growth media or not.

Disclosed kits can also optionally include a detector. Detectors, such as photomultiplier tubes, avalanche photodiodes, charge coupled devices (CCDs), photodiodes, or other active devices for example, may be utilized. The detector can also be combined with or used in combination with various filters and optics as are commonly utilized. A detector that can be optionally included in disclosed kits can be capable of detecting one or more than one wavelength of emitted light. Alternatively, more than one detector can optionally be included.

Disclosed kits can also optionally include other components including for example imaging components (for example for imaging the detected emitted light), processor(s), or sample collection or preparation aids. In embodiments, one or more processors can be utilized or configured to process images from imaging components to clean up the images or automatically count colonies; to provide output indicating the presence or absence of microorganisms in the test sample; to control a light source(s), detector(s), optional components, or some combination thereof; or some combination thereof.

Disclosed kits can be configured to work in concert with or can be included along with currently utilized systems such as the 3M™ Petrifilm™ product line, the 3M™ Attest™ Biological Monitoring System, the SPECTRA MAX M5 (Molecular Devices, Sunnyvale, Calif.), and the 3M™ Clean-Trace™ System (3M Co., St. Paul, Minn.).

In embodiments of disclosed kits, the fluorescently detectable product can be a coumarin derivative. In embodiments, the fluorescently detectable product can be 4-methylumbelliferone and $Ex\lambda$iso (the wavelength the light source is capable of generating) can be about 330 nm. In embodiments, the fluorescently detectable product can be 3-cyano-7-hydroxycoumarin and $Ex\lambda$iso (the wavelength the light source is capable of generating) can be about 375 nm. In embodiments, the fluorescently detectable product can be 7-hydroxycoumarin-3-carboxylic acid ester and $Ex\lambda$iso (the wavelength the light source is capable of generating) can be about 370 nm. In embodiments, the fluorescently detectable product can be 3-(2-thienyl)umbelliferone and $Ex\lambda$iso (the wavelength the light source is capable of generating) can be about 380 nm.

EXAMPLES

Materials and Methods

Unless otherwise noted, all chemicals were obtained from Aldrich and were used without further purification.

All parts, percentages, ratios, etc. in the examples are by weight, unless noted otherwise. Solvents and other reagents used were obtained from Sigma-Aldrich Chemical Company; Milwaukee, Wis. unless indicated unless specified differently.

Materials 7-hydroxycoumarin-3-carboxylic acid ethyl ester (EHC) was prepared according to Chilvers et. al. J. Appl. Microbiology 2001, 91, 1118-1130.

3-(2-thienyl)umbelliferone (TU) was prepared as in U.S. Pat. No. 6,372,895 (Bentsen et al.).

3-(2-thienyl)umbelliferone galactoside (TUgal) was prepared as in U.S. Pat. No. 6,372,895 (Bentsen et al.).

β-D-galactosidase was acquired from EMD Biosciences, Inc. (San Diego, Calif.).

Example 1

4-methylumbelliferone (4-MU) was dissolved in dimethyl sulfoxide (DMSO) at a concentration of 1 mg/mL. A 96-well plate was prepared with each well containing 100 μL of 100 mmolar phosphate buffer at pH values ranging from 8.0 down to 2.5. 10 μL of the 4-MU solution was added to each of the wells. A set of 10× diluted wells were also prepared to eliminate artifacts due to self-quenching of the fluorophore at high concentrations. The 10× diluted wells were prepared by diluting the 1 mg/mL solution to 0.1 mg/mL with DMSO and then adding 10 μL of this solution to 100 μL of 100 mmolar phosphate buffer in each of the wells.

Absorption spectra from 250 to 500 nm were recorded using a SPECTRAMAX M5 (available from Molecular Devices, Sunnyvale, Calif.) fluorescence plate reader. The results for the absorption spectra are shown FIG. 1A. These results demonstrated that the absorption of the neutral 4-MU species (formed at a low pH) is low at wavelengths near the absorption maxima for the anion (formed at a high pH). The absorption maximum of the neutral 4-MU occurs at about 320 nm and there is an isosbestic point (where absorbance is invariant with composition) at about 330 nm.

Emission at various wavelengths was also measured with the SPECTRAMAX M5 fluorescence plate reader. FIG. 1C shows the resulting emission for the 10× diluted samples as a function of emission wavelength for an excitation wavelength of 331 nm and for various pH values. These results demonstrate that excitation near the isosbestic point (about 330 nm) provides a fluorescent response that is largely invariant with pH value over the range studied (2.5 to 8). The maximum emission occurred at a wavelength of 450 nm.

For comparison, emission was also measured as a function of pH value for an excitation wavelength of 360 nm, which is near the maximum absorption wavelength for the anion. FIG. 1B shows emission at about 450 nm as a function of pH for an excitation wavelength of 360 nm and 331 nm (approximately at the isosbestic point).

Example 2

96-well plates were prepared as in Example 1, but with 3-cyano-7-hydroxycoumarin (CyU) substituted for 4-MU. Absorption and emission spectra were measured as in Example 1.

Figure 5A:
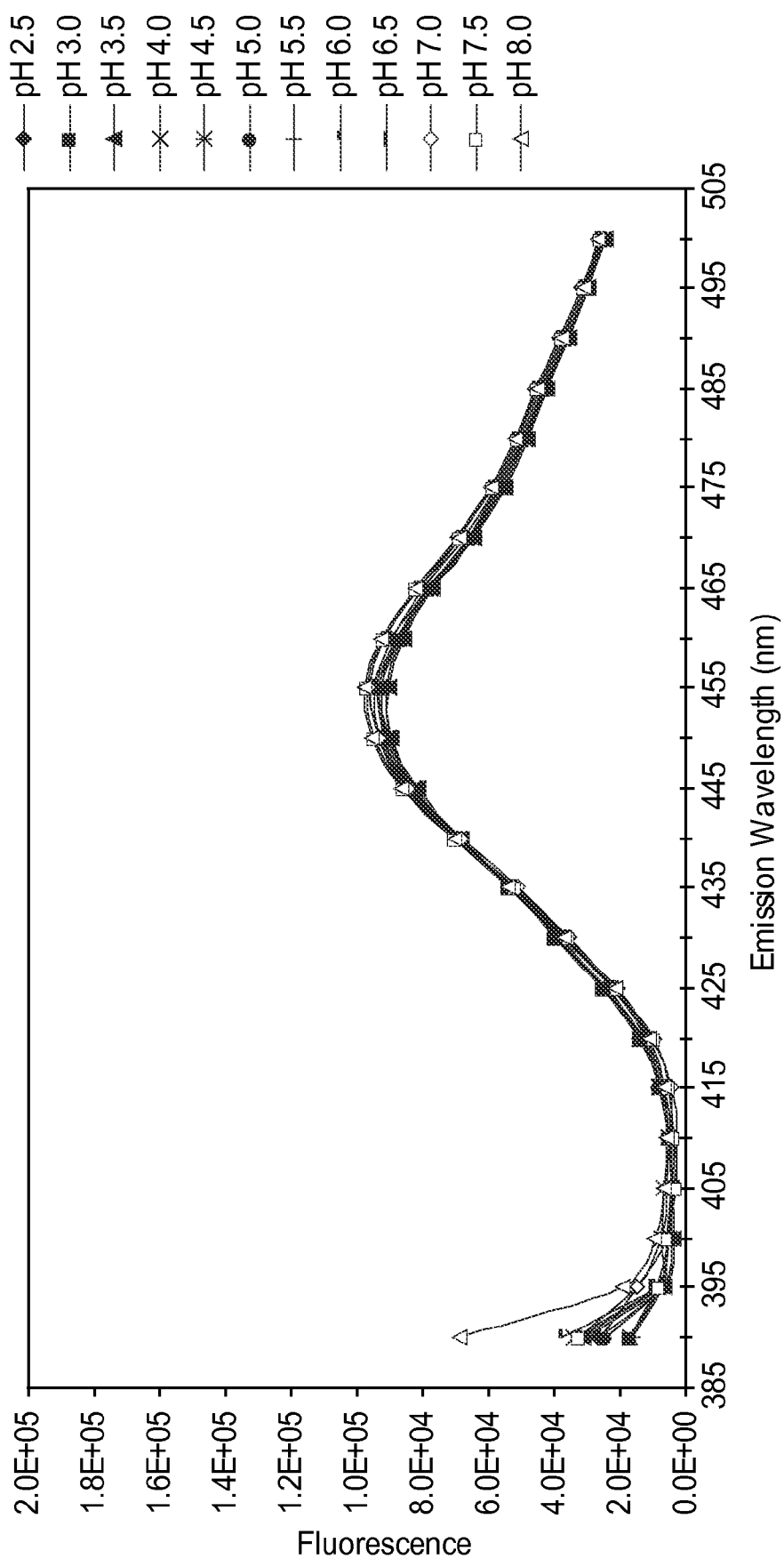
FIGS. 5A, 5B, and 5C are an emission spectra (375 nm) as a function of pH (FIG. 5A), an emission spectra (455 nm) as a function of pH at three different excitation wavelengths (FIG. 5B), and a plot of the ratios of peak emissions for excitation at different wavelengths (FIG. 5C)
Figure 5B:
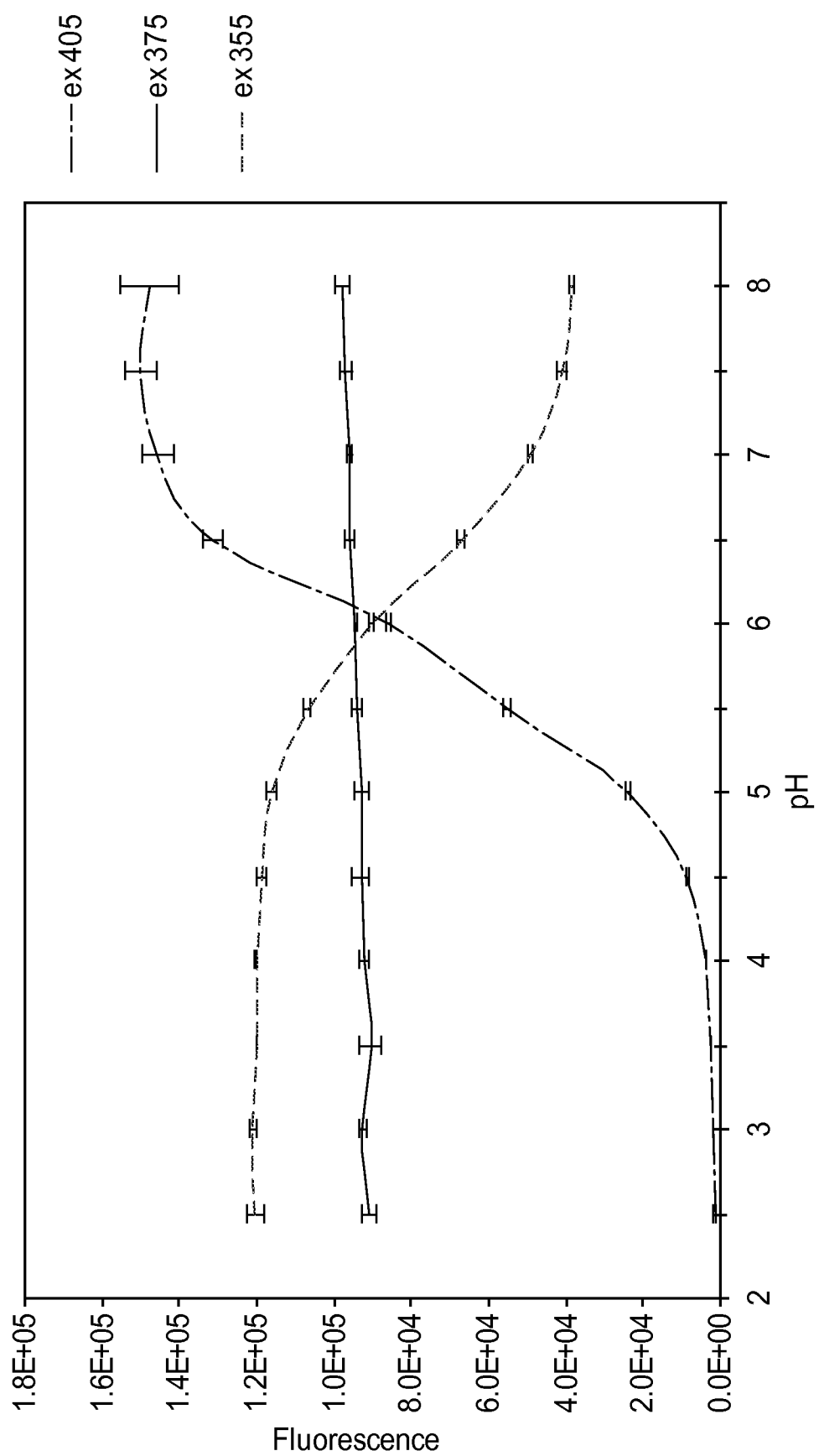

Absorption spectra of CyU at various pH values were obtained (not shown). Emission spectra were determined at various pH values for CyU at three different excitation wavelengths, corresponding to the maximum absorbance of the neutral species (355 nm), the isosbestic point (375 nm) (shown in FIG. 5A) or the anion absorbance maximum (405 nm). The wavelength of maximum emission was about 455 nm when the excitation wavelength was 375 nm. FIG. 5B shows emission at a wavelength of 455 nm as a function of pH value for excitation wavelengths of 355 nm, 375 nm (approximately at the isosbestic point), and 405 nm. The fluorescence was approximately independent of pH value when the excitation was at the isosbestic point.

Figure 5C:
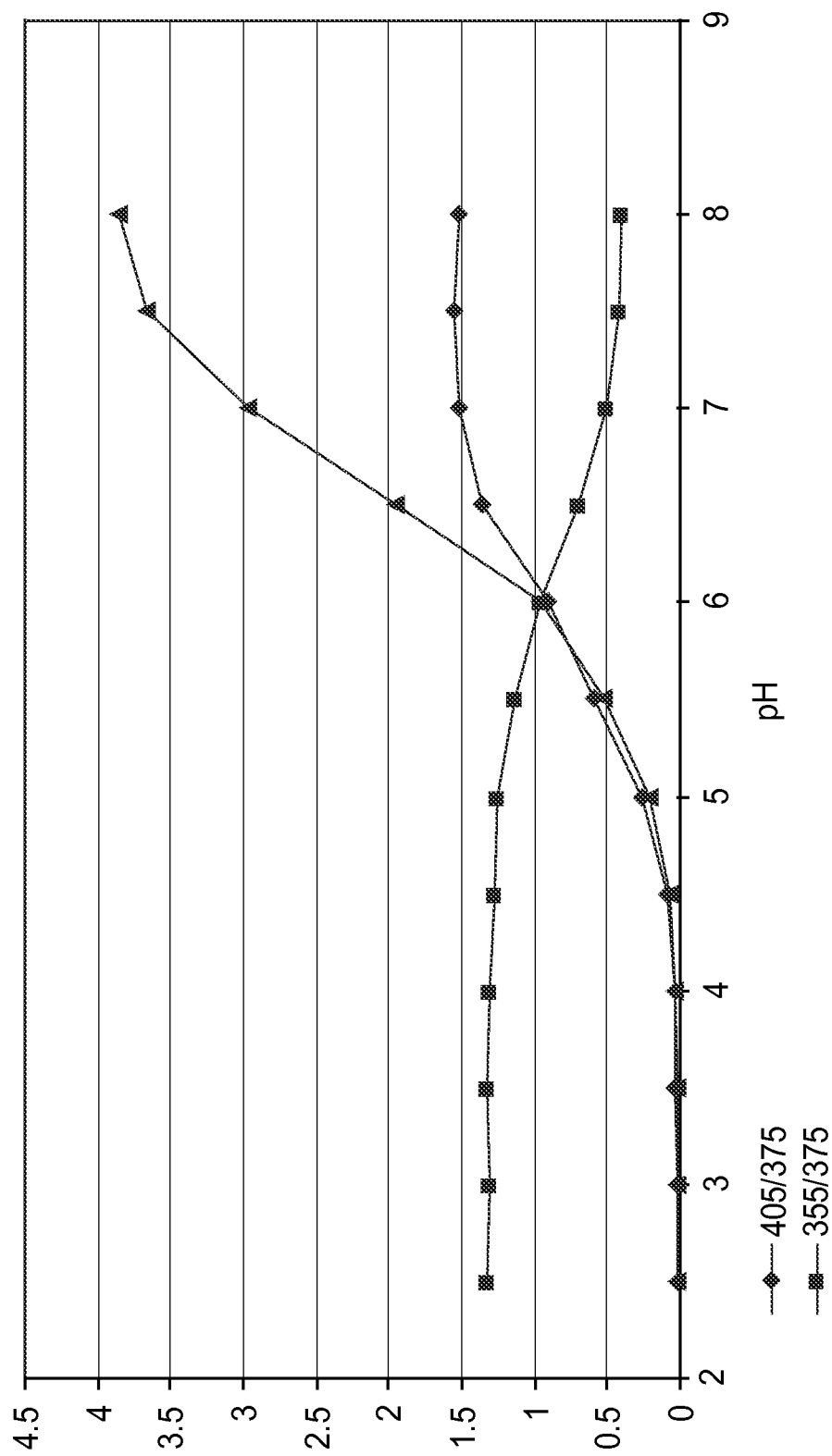

The ratio of the peak emission intensity recorded at different excitation wavelengths was determined. As shown in FIG. 5C, this yields a dimensionless number that is sensitively dependent upon pH. This provides a sensitive pH response that does not depend on measuring absolute fluorescent intensity.

Example 3

7-hydroxycoumarin-3-carboxylic acid ethyl ester (EHC) was dissolved in dimethyl sulfoxide (DMSO) at a concentration of 1 mg/mL. A 96-well plate was prepared with each well containing 100 μL of 100 mmolar phosphate buffer at pH values ranging from 8.0 down to 2.5. 10 μL of the EHC solution was added to each of the wells. 10× diluted wells were prepared by taking 10 μL of the wells prepared at the initial concentration, and adding this to 90 μL of buffer at the appropriate concentration. Absorption and emission spectra were measured as in Example 1.

Figure 6:
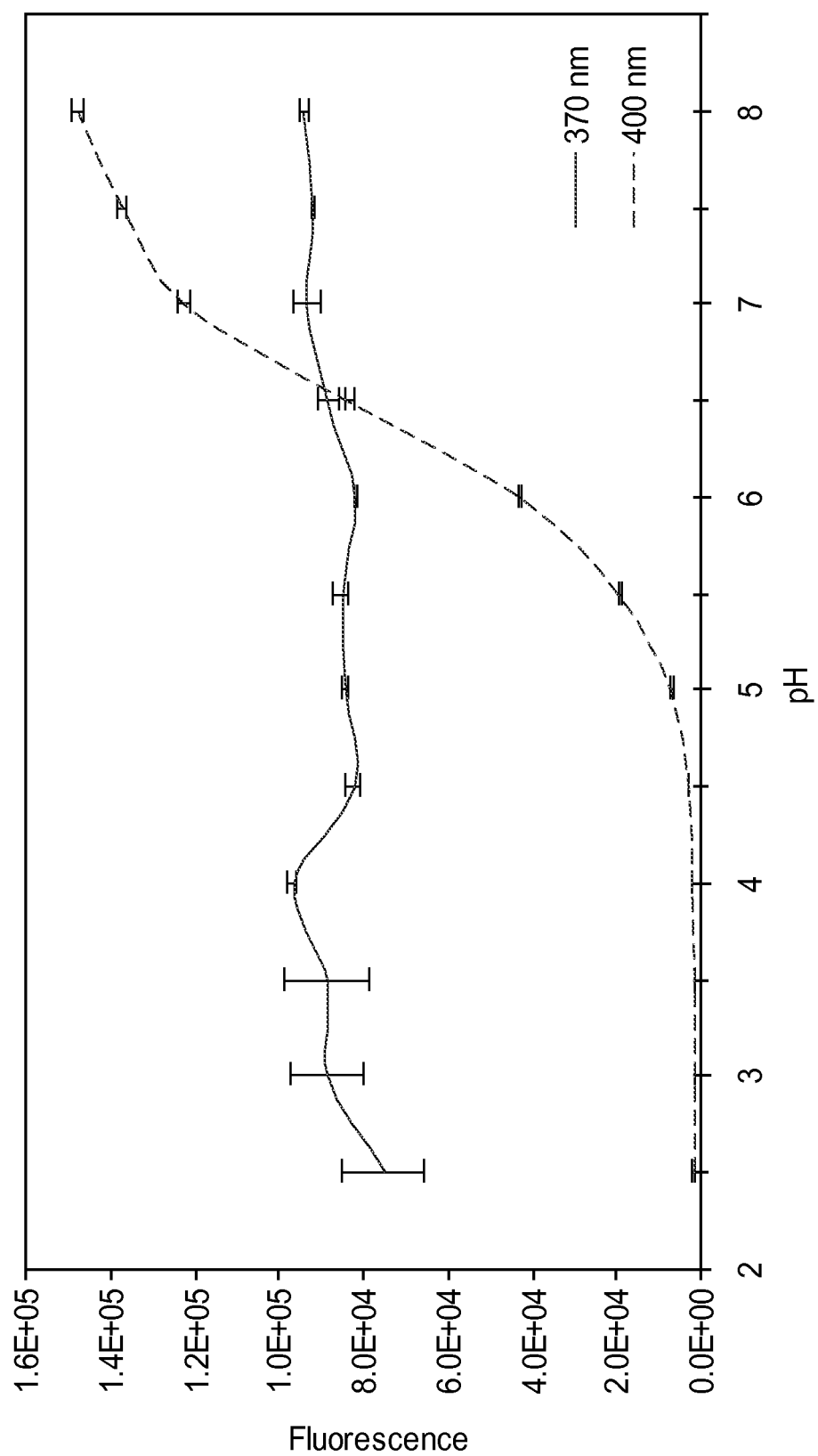
FIG. 6 is an emission (450 nm) spectra for 7-hydroxycoumarin-3-carboxylic acid ethyl ester (EHC) as a function of pH.

Absorption spectra of EHC at various pH values were obtained (not shown). The isosbestic point was found to occur at about 370 nm. The fluorescence as a function of pH for the 10× diluted EHC samples are shown in FIG. 6 with an excitation wavelength of 370 nm and, for comparison, with an excitation wavelength of 400 nm (anion maximum absorbance). The fluorescence was approximately constant when excited at the isosbestic point.

Example 4

96-well plates were prepared as in Example 1, but with 3-(2-thienyl)umbelliferone (TU) substituted for 4-MU. TU is described in U.S. Pat. Nos. 6,372,895 (Bensten et al.) and 6,566,508 (Bensten et al.) which are hereby incorporated herein by reference. Absorption and emission spectra were measured as in Example 1, 2, and 3.

Figure 7A:
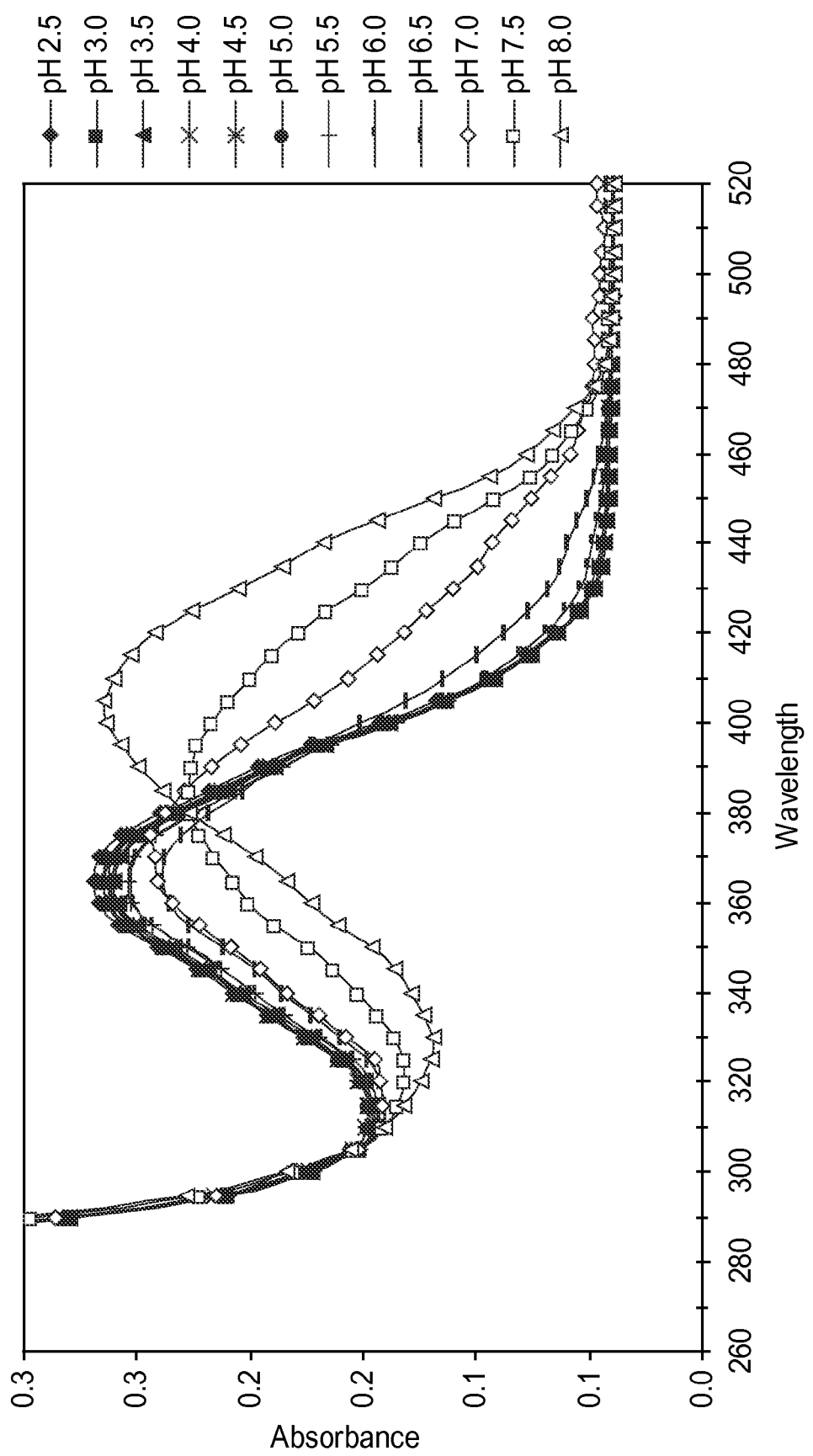
FIGS. 7A, 7B, and 7C are an absorption spectra of 3-(2-thineyl)umbelliferone (TU) for different pH values (FIG. 7A), 380 nm (FIG. 7B), and emission (at 500 nm) upon excitation at 405 nm and emission (at 490 nm) upon excitation at 380 nm as a function of pH (FIG. 7C)

Absorption spectra of the 10×TU samples at various pH values are shown in FIG. 7A. The isosbestic point was found to occur at about 380 nm. The absorption peaks were generally 5-10 nm red-shifted compared to CyU and EHC.

Figure 7B:
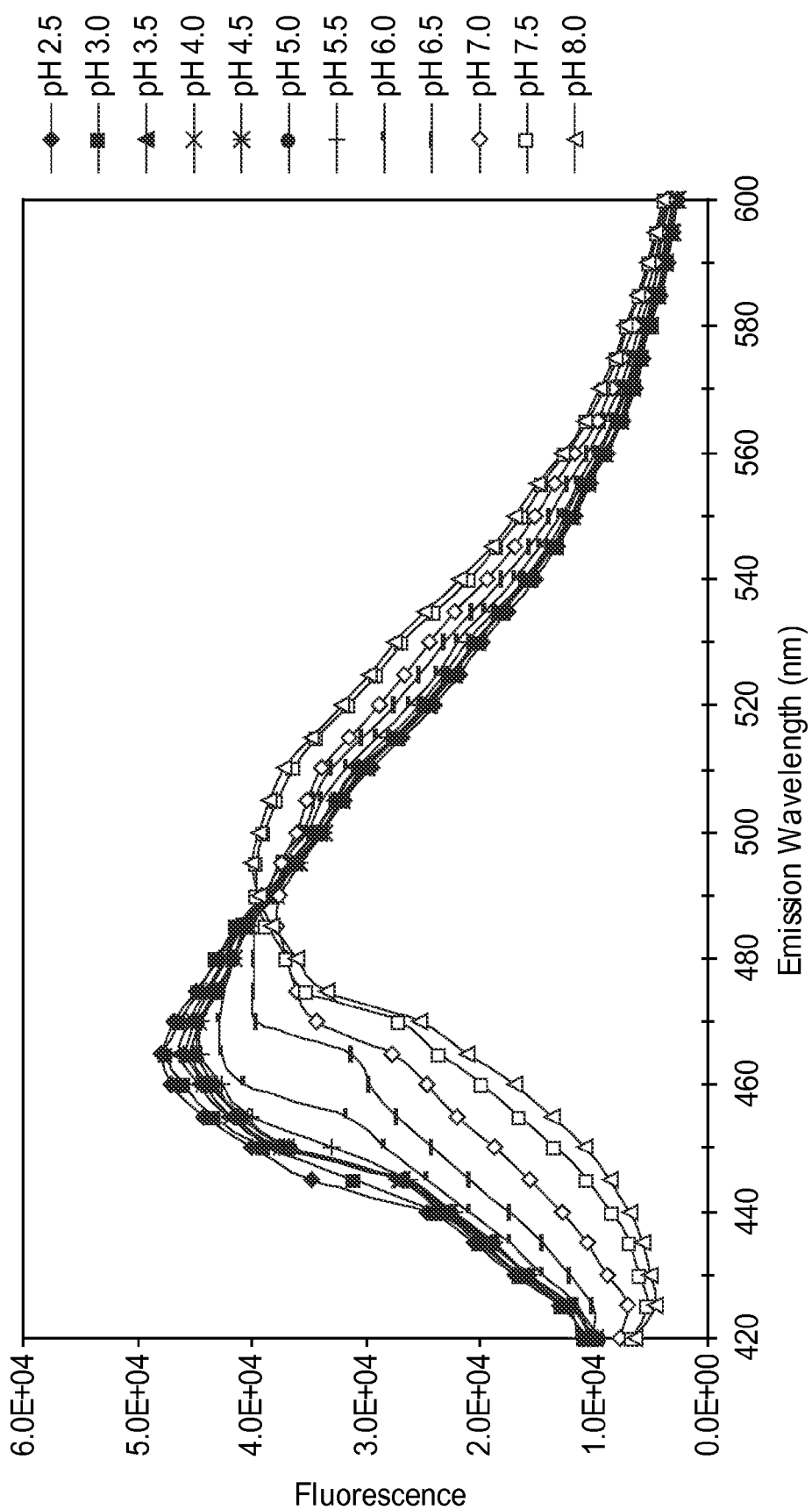

Emission spectra were obtained for various pH values for TU at three different excitation wavelengths, 405 nm (anion maximum, for comparison), 380 nm (isosbestic point—shown in FIG. 7B), and 365 nm (neutral species maximum, for comparison). The anion emission band was red-shifted 40 nm to about 495 nm compared to 455 nm for Examples 1 and 2. The Stokes shift for the anionic species was determined to be approximately 90 nm.

When samples at low pH were excited at 405 nm (anion maximum absorbance) the emission at 495 nm diminished and the peak maximum was blue-shifted about 30 nm to 465 nm. The blue shift was more apparent when the excitation wavelength was set to the isosbestic point (380 nm, FIG. 7B) or the neutral species maximum (365 nm). These results indicate that at low pH values, there is pronounced emission from the excited state of the neutral TU, in addition to that from the photogenerated anion.

Figure 7C:
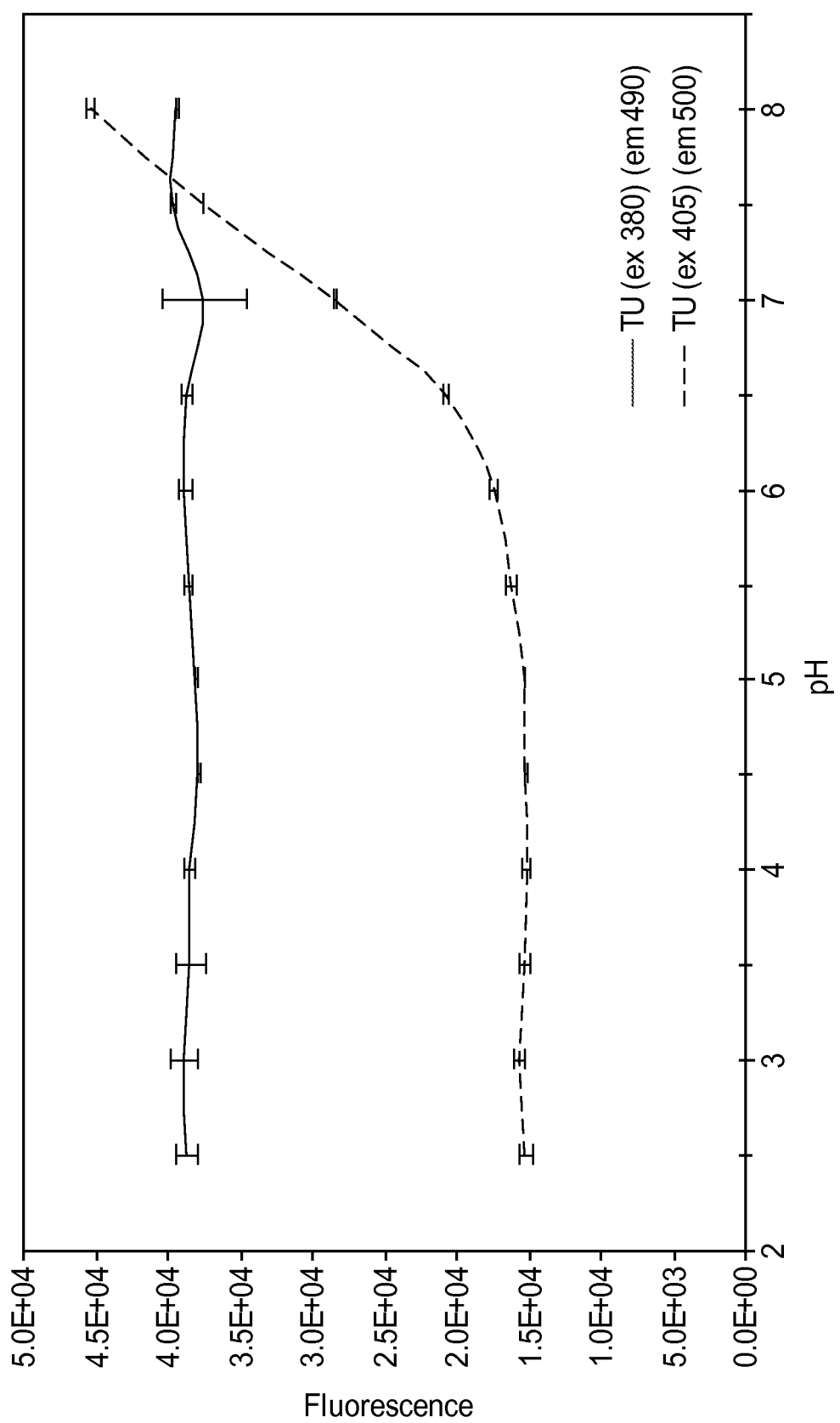

Although there was variation in the emission spectra with varying pH values when TU was excited at the isosbestic point for absorption, there was an isosbestic point for emission (about 490 nm, see FIG. 7B) where the emission did not depend on the pH. The fluorescence as a function of pH for the TU samples are shown in FIG. 7C for excitation wavelengths of 380 nm and 405 nm and for emission wavelengths of 490 nm and 500 nm. The fluorescence was approximately independent of pH when excited at the absorption isosbestic point (380 nm) and measured at the emission isosbestic point (490 nm).

Example 5

4-methylumbelliferone phosphate disodium salt (4-MUP) was dissolved in water at a concentration of 1 mg/mL. A 96-well plate was prepared with each well containing 100 μL of 100 mmolar phosphate buffer at pH values ranging from 8.0 down to 2.5. 10 μL of the MUP solution was added to each of the wells. A set of 10× diluted wells were also prepared to eliminate artifacts due to self-quenching of the fluorophore at high concentrations. The 10× diluted wells were prepared by diluting the 1 mg/mL solution to 0.1 mg/mL with water and then adding 10 μL of this solution to 100 μL of 100 mmolar phosphate buffer in each of the wells. Absorption and emission spectra were measured as in Example 1.

It was found that 4-MUP had noticeable absorption at the isosbestic point of the 4-MU dye (about 330 nm), but minimal absorption at the anion maximum (about 360 nm). The MUP absorption spectrum showed little pH-dependence and the absorption at the isosbestic point was only about ¼ to % of that of the free dye.

The maximum emission occurred at about 390 nm for the range of pH values considered. The emission was very small at the characteristic emission wavelength of 4-MU (455 nm). This means that the presence of unreacted 4-MUP would not significantly increase the background signal when the presence of 4-MU is measured.

Example 6

4-methylumbelliferone-β-D-galactoside (4-MUG) was dissolved in dimethyl sulfoxide (DMSO) at a concentration of 0.1 mg/mL. A 96-well plate was prepared with each well containing 100 μL of 100 mmolar phosphate buffer at pH values ranging from 2.5 (column 1) up to 8.0 (column 12). 10 μL of the 4-MUG solution was added to each well in the first four rows. Two of these rows were further treated with 10 μL of a reagent solution containing mercaptoethanol (1.4% v/v), MgCl$_2$ (2% w/w) and (3-D-galactosidase (80 μg/mL). 10 μL of a 0.1 mg/mL solution of 4-MU in DMSO was added to two more rows for comparison. Absorption and emission spectra were measured as in Example 1.

The absorption spectra of 4-MUG with and without galactosidase were obtained. The spectrum of 4-MUG in the absence of added (3-D-galactosidase showed little pH-dependence and was similar to that of 4-MU in acid solution, i.e.: that of the neutral 4-MU. Consequently 4-MUG absorbs strongly at the isosbestic point of 4-MU dye (about 330 nm), but minimally at the anion maximum (about 360 nm).

The emission spectra (335 nm excitation) for 4-MUG in the absence and presence of β-D-galactosidase were also obtained for pH values from 2.5 to 8. The maximum emission was low and occurred at about 390 nm in the absence of enzyme, with very little intensity at the characteristic emission wavelength of 4-MU (455 nm). In the presence of the β-D-galactosidase enzyme, an emission peak was observed at 455 nm corresponding to emission from the free 4-MU anion.

Figure 8A:
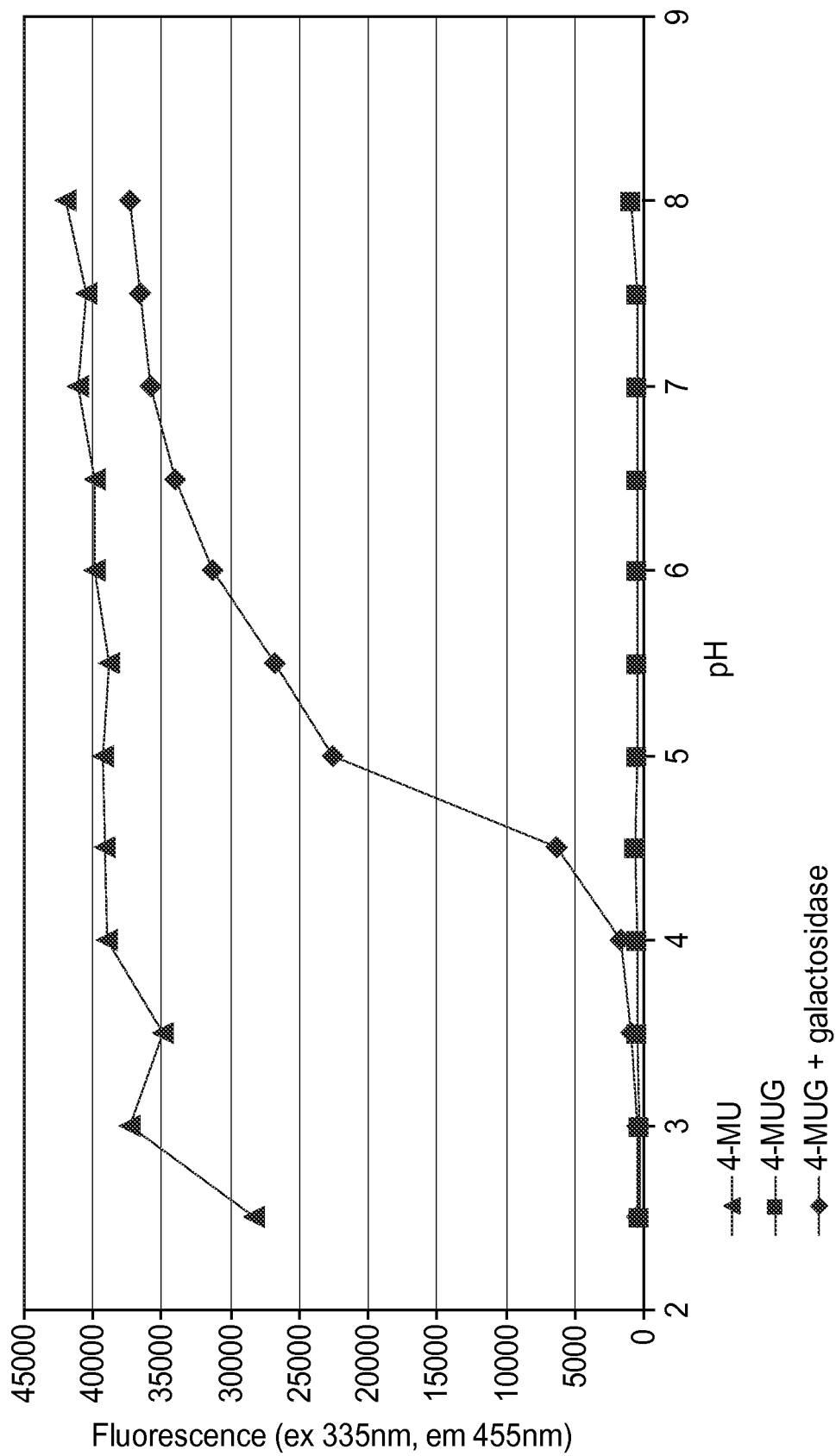
FIGS. 8A, and 8B are emission (at 455 nm) upon excitation at 335 nm as a function of pH for 4-MU and 4-MUG in the presence and absence of β-D-galactosidase (FIG. 8A), and emission (at 455 nm) upon excitation at 360 nm as a function of pH for 4-MU and 4-MUG in the presence and absence of β-D-galactosidase (FIG. 8B)
Figure 8B:
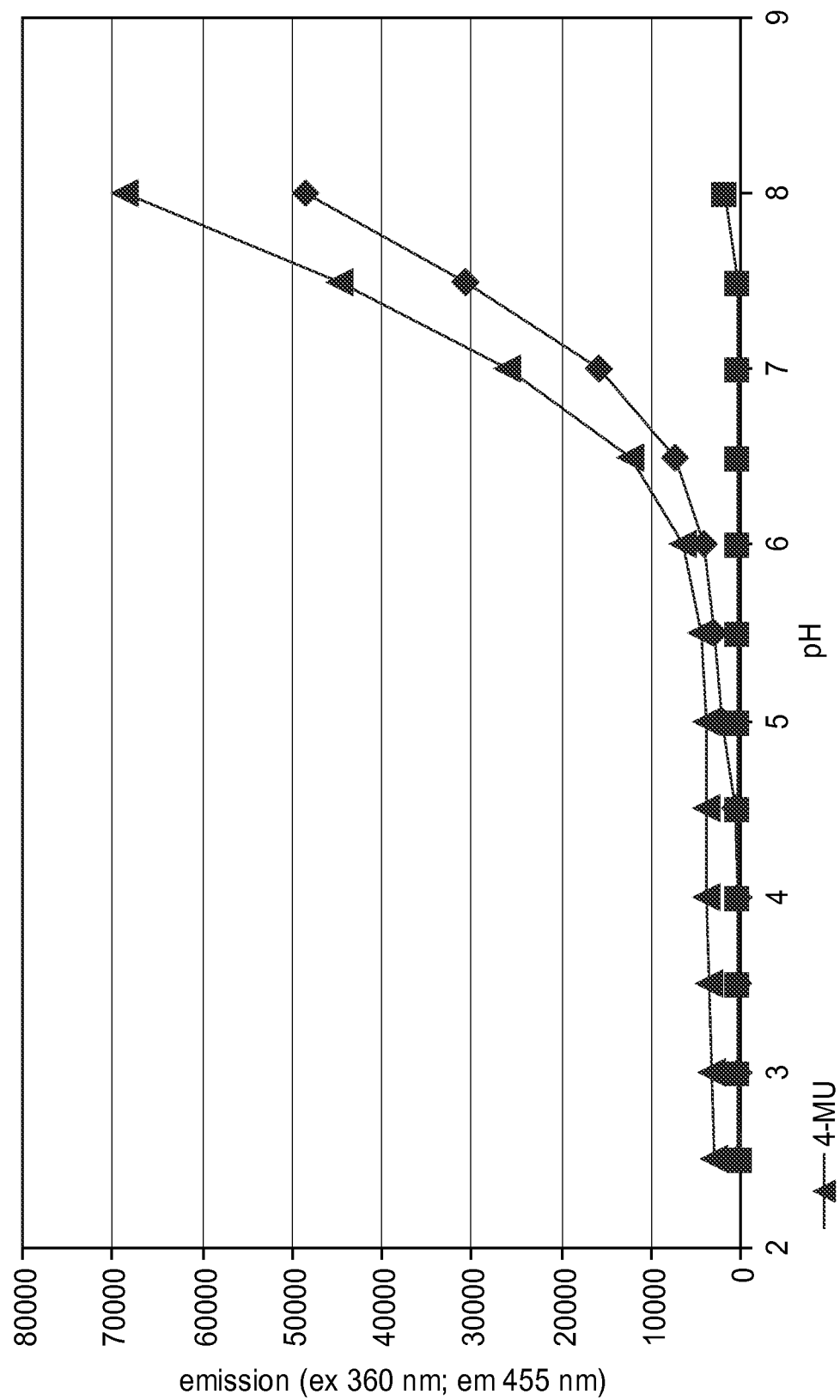

The emission at 455 nm (with an excitation at the isosbestic wavelength of 355 nm) for 4-MU, as well as 4-MUG in the absence and presence of β-D-galactosidase is shown in FIG. 8A as a function of pH. The emission for 4-MUG+β-D-galactosidase falls off slowly below pH 7, consistent with the reported activity of the enzyme (Sungur and Akbulut, *J. Chem. Tech Biotechnol.* 1994, 59, 303-306). Nevertheless, useful intensity was observed at least as low as pH 5. For comparison, emission resulting from excitation at the anion maximum (about 360 nm) is shown in FIG. 8B. In this case, emission was very low at acidic pH values and increased rapidly above pH 7.

This example demonstrated the ability to use MUG to effectively detect β-D-galactosidase over a wide range of pH values without adjusting excitation or emission frequencies by exciting at the isosbestic point of the dye.

Example 7

Methyl 7-hydroxycoumarin-3-carboxylate galactoside (MHCgal) was prepared by reacting EHC with α-acetobromo-D-galactose and then hydrolyzing the protected galactoside with sodium methoxide, as described in Chilvers (*J. Appl. Microbiology* 2001, 91, 1118-1130). MHCgal was dissolved in dimethyl sulfoxide (DMSO) at a concentration of 1.0 mg/mL, and then 10 μL put in each well of a 96-well plate prepared with wells containing 100 μL of 100 mmolar phosphate buffer at pH levels ranging from 8.0 down to 2.5. Half of the rows were further treated with 10 μL of a reagent solution containing mercaptoethanol (1.4% v/v), MgCl$_2$ (2% w/w) and β-D-galactosidase (80 μg/mL). 10 μL from each well of this plate was then added to the corresponding well of another plate containing 100 μL of the phosphate buffer with the appropriate pH in the wells creating a 10× dilution plate. Absorption and emission spectra were measured as in Example 1.

The absorption spectra of MHCgal with and without β-D-galactosidase were obtained. The spectrum of MHCgal in the absence of added β-D-galactosidase showed no pH-dependence over the pH range tested, and demonstrated a maximum absorbance at about 340 nm. With added β-D-galactosidase, the absorption shifted to 350 nm for pH 5-6 and to 400 nm for alkaline values. These are consistent with the absorption maxima for the neutral and anionic EHC species.

The emission spectra for MHCgal (with an excitation wavelength of 370 nm) in the absence and presence of β-D-galactosidase were obtained for pH values from 2.5 to 8. The emission was low without enzyme, with very little emission at the characteristic emission wavelength of simple comuarins (~450 nm). In the presence of the β-D-galactosidase enzyme, a strong emission peak was observed at 445 nm corresponding to emission from free MHC anion.

Figure 9:
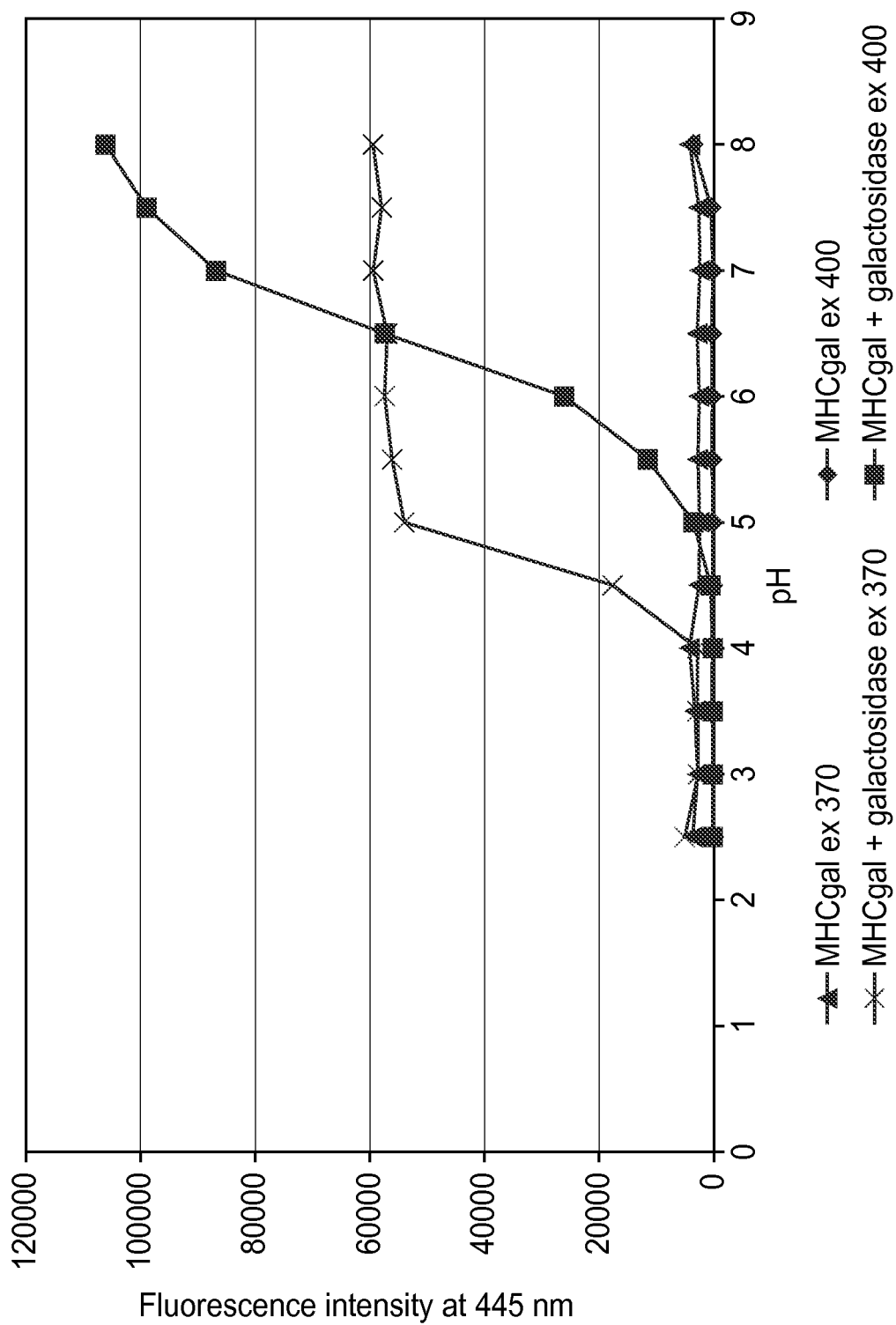
FIG. 9 is emission at 445 nm (excitation 370 nm or 400 nm) as a function of pH for MHCgal in the presence and absence of β-D-galactosidase.

The emission at 445 nm (for excitation at the 370 nm isosbestic point, and, for comparison, for excitation at the anion maximum at 400 nm) for MHCgal in the absence and presence of β-D-galactosidase is shown in FIG. 9 as a function of pH. In the presence of β-D-galactosidase, the emission of MHCgal when excited at 370 nm is substantial and constant from a pH of about 5 and higher. In contrast, the excitation at the anion maximum resulted in emission that was very low at low pH values but increased steeply from pH 6.

This example demonstrated the ability to use MHCgal to effectively detect β-D-galactosidase over a wide range of pH values without adjusting excitation or emission frequencies by exciting at the isosbestic point of the dye.

Comparative Example 8

3-(2-thienyl)umbelliferone galactoside (TUgal) was dissolved in dimethyl sulfoxide (DMSO) at a concentration of 0.1 mg/mL. A 96-well plate was prepared with wells containing 100 μL of 100 mmolar phosphate buffer at pH levels ranging from 8.0 down to 2.5. 10 μL of the TUgal solution was added to each of the wells, and then half of the rows were further treated with 10 μL of a reagent solution containing mercaptoethanol (1.4% v/v), $MgCl_2$ (2% w/w) and β-galactosidase (80 μg/mL). Absorption and emission spectra were measured as in Example 1.

Figure 10:
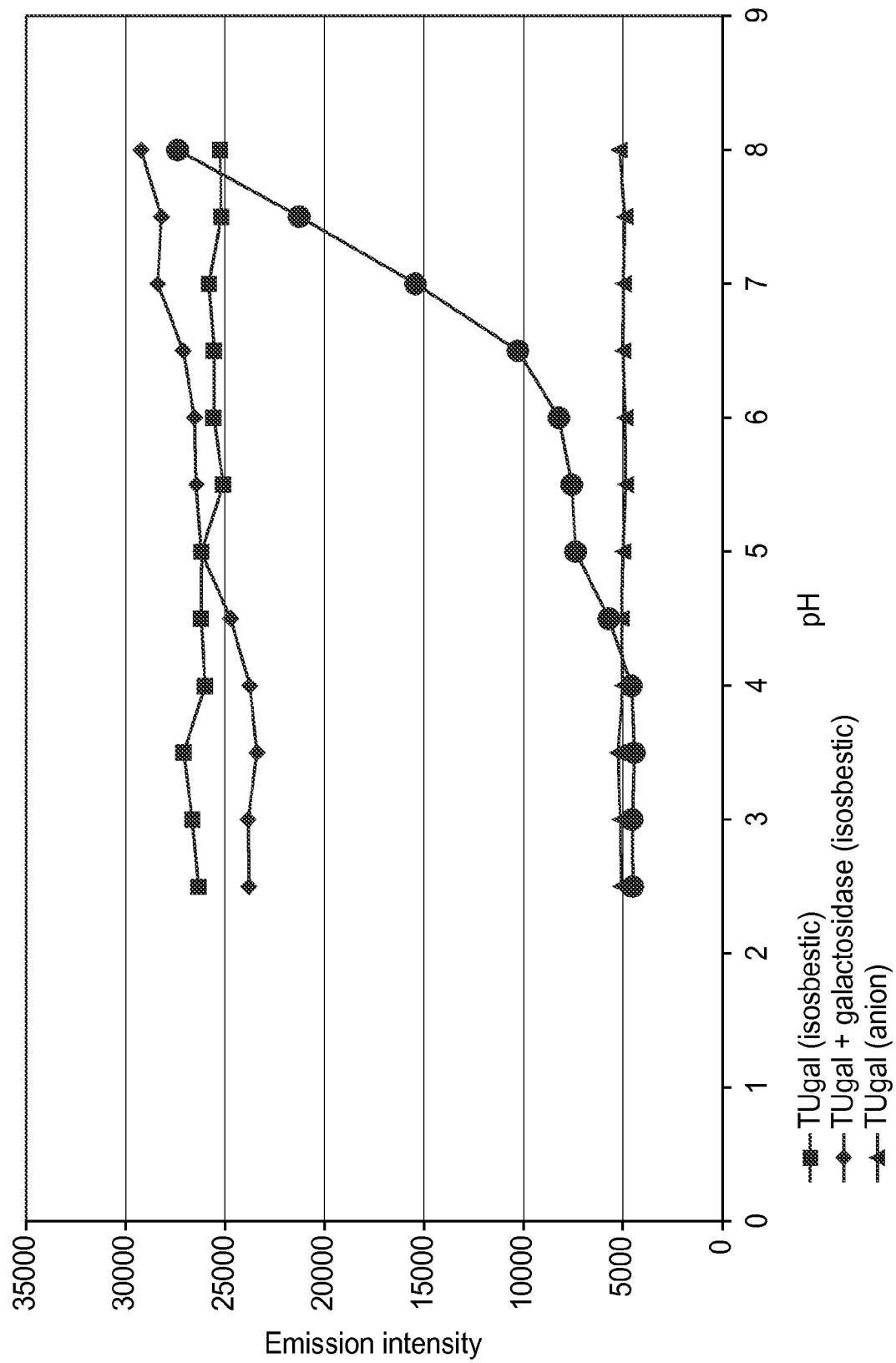
FIG. 10 is emission at 490 nm upon excitation at 380 nm as a function of pH for 3-(2-thienyl)umbelliferone-β-D-galactopyranoside (TUgal) in the presence and absence of β-D-galactosidase, and emission at 500 nm upon excitation at 410 nm as a function of pH for TUgal in the presence and absence of β-D-galactosidase.

The emission for TUgal at 490 nm (380 nm excitation) and 500 nm (410 nm excitation) in the presence and absence of β-D-galactosidase is shown in FIG. 10 as a function of pH. When measured at the isosbestic frequencies for TU (380 ex, 490 em; see Example 4) TUgal possessed comparable emission to TU, the product fluorophore itself. Thus there was little difference between emission in the presence or absence of enzyme. The measurement of fluorescence near the anion maxima (ex 410 nm, em 500 nm) reduced the emission of the enzyme substrate well below that of the anion and enabled the use of TUgal as a β-D-glactosidase substrate.

As seen in this example, irradiation at the isosbestic excitation frequency can be less effective in situations where it causes the enzyme substrate to emit strongly at the same frequencies as the free fluorophore.

Thus, embodiments of methods of detecting microorganisms and kits therefore are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. A method of determining the amount of microorganisms present in a test sample, the method comprising the steps of:
   a) incubating the test sample with enzyme substrate to form an incubated sample, wherein the enzyme substrate comprises an enzymatically hydrolysable group and a fluorescent group, wherein microorganisms present in the test sample include an enzyme that hydrolyzes the hydrolysable group from the fluorescent group to form a fluorescently detectable product, and wherein the fluorescently detectable product has both an acidic and basic species;
   b) exciting the fluorescently detectable product with light having a wavelength of Exλiso for a time sufficient for the fluorescently detectable product to emit light, wherein Exλiso is the absorbance isosbestic point of the fluorescently detectable product;
   c) detecting light emitted at a wavelength of Emλ1; and
   d) quantifying the light emitted at the wavelength of Emλ1, wherein the quantity of the light emitted at the wavelength Emλ1 is indicative of the amount of microorganisms present in the incubated test sample, wherein the quantity of the light emitted at the wavelength Emλ1 is substantially constant across a pH range of 2.5 to 8.0.

2. The method according to claim 1, wherein the pH of the incubated sample is not adjusted before the excitation and detection steps.

3. The method according to claim 1 further comprising exciting the fluorescently detectable product with light having a wavelength of Exλ2 for a time sufficient for the fluorescently detectable product to emit light, wherein Exλ2 is the absorption maximum of the basic species of the fluorescently detectable product or the absorption maximum of the acidic species of the fluorescently detectable product.

4. The method according to claim 3 further comprising determining the ratio of the emission caused by excitation at Exλiso and the emission caused by excitation at Exλ2, wherein the ratio is indicative of the amount of microorganisms present in the test sample.

5. The method according to claim 1, wherein the fluorescently detectable product is a coumarin derivative.

6. The method according to claim 1, wherein the fluorescently detectable product is 4-methylumbelliferone and Exλiso is about 330 nm.

7. The method according to claim 1, wherein the fluorescently detectable product is 3-cyano-7-hydroxycoumarin and Exλiso is about 375 nm; the fluorescently detectable product is 7-hydroxycoumarin-3-carboxylic acid ethyl ester and Exλiso is about 370 nm; or the fluorescently detectable product is 7-hydroxycoumarin-3-carboxylic acid methyl ester and Exλiso is about 370 nm.

8. The method according to claim 1, wherein the fluorescently detectable product is 3-(2-thienyl)umbelliferone and Exλiso is about 380 nm.

9. The method according to claim 1, wherein the step of incubating the test sample with the enzyme substrate comprises adding the sample in a liquid form to a dehydrated growth media containing the enzyme substrate.

10. The method according to claim 1 further comprising forming an image of the detected light.

11. The method according to claim 10 further comprising counting colonies from the image.

12. The method according to claim 1, wherein Emλ1 is the wavelength at the maximum fluorescence of the fluorescently detectable product.

13. The method according to claim 1 further comprising quantifying the light emitted near a wavelength Emλ2, wherein Emλ1 and Emλ2 are different wavelengths, and further comprising determining a ratio of the light emitted at a wavelength Emλ1 and the light emitted at a wavelength Emλ2, wherein the ratio is indicative of the amount of microorganisms present in the test sample.

14. The method of claim 13, wherein the wavelength Emλ2 is the wavelength of the isosbestic emission point.

15. The method of claim 13, wherein the amount of light emitted by the fluorescently detectable product near the wavelength Emλ2 is substantially greater than the amount of any light emitted by the enzyme substrate near the wavelength Emλ2.

16. A method of determining the amount of microorganisms present in a test sample, the method comprising the steps of:
   a) incubating the test sample with an enzyme substrate to form an incubated sample, wherein the enzyme substrate comprises an enzymatically hydrolysable group and a fluorescent group, wherein microorganisms present in the test sample include an enzyme that hydrolyzes the hydrolysable group from the fluorescent group to form a fluorescently detectable product, and wherein the fluorescently detectable product has both an acidic and basic species;

b) exciting the fluorescently detectable product with light having a wavelength of Ex$\lambda$iso for a time sufficient for the fluorescently detectable product to emit light, wherein Ex$\lambda$iso is the isosbestic point of the fluorescently detectable product;

c) detecting light emitted at a wavelength of Em$\lambda$1 as a result of the excitation with light having a wavelength of Ex$\lambda$iso;

d) exciting the fluorescently detectable product with light having a wavelength of Ex$\lambda$2 for a time sufficient for the fluorescently detectable product to emit light, wherein Ex$\lambda$2 is the absorption maximum of the basic species of the fluorescently detectable product or the absorption maximum of the acidic species of the fluorescently detectable product;

e) detecting light emitted at a wavelength of Em$\lambda$1 as a result of the excitation with light having a wavelength of Ex$\lambda$2; and f) calculating a ratio based on the light emitted at a wavelength of Em$\lambda$1 as a result of the Ex$\lambda$iso excitation light and the light emitted as a result of the Ex$\lambda$2 excitation light, wherein the ratio is indicative of the amount of microorganisms present in the test sample.

17. The method according to claim 16, wherein Ex$\lambda$2 is the absorption maximum of the acidic species of the fluorescently detectable product.

18. The method according to claim 16, wherein the ratio can be utilized to monitor the pH of the incubated sample over time.

* * * * *

UNITED STATES PATENT AND TRADEMARK OFFICE
CERTIFICATE OF CORRECTION

PATENT NO. : 8,518,664 B2  
APPLICATION NO. : 13/513794  
DATED : August 27, 2013  
INVENTOR(S) : Stephen Barrie Roscoe et al.

Page 1 of 1

It is certified that error appears in the above-identified patent and that said Letters Patent is hereby corrected as shown below:

On the Title Page, in Column 2, under Item (57) (Abstract)
Line 6, delete "hydrolyzable" and insert -- hydrolysable --, therefor.
Line 8, delete "hydrolyzable" and insert -- hydrolysable --, therefor.

In the Specifications

Column 2
Line 62, delete "thineyl" and insert -- thienyl --, therefor.

Column 4
Line 17, delete "Organella" and insert -- Morganella --, therefor.

Column 6
Line 2, delete "L-hydroxproline," and insert -- L-hydroxyproline, --, therefor.
Line 23, delete "naphtalene" and insert -- naphthalene --, therefor.
Lines 25-26, delete "tetrapyroole" and insert -- tetrapyrrole --, therefor.

Column 17
Line 40, delete "%" and insert -- 1/3 --, therefor.
Line 59, delete "(3-" and insert -- β- --, therefor.
Line 65, delete "(3-" and insert -- β- --, therefor.

Column 18
Line 59, delete "comuarins" and insert -- coumarins --, therefor.

Column 19
Line 32, delete "glactosidase" and insert -- galactosidase --, therefor.

Signed and Sealed this
Fourth Day of February, 2014

Michelle K. Lee
*Deputy Director of the United States Patent and Trademark Office*